UNITED STATES PATENT

US 7,803,826 B2
Tachibana et al.
Date of Patent: *Sep. 28, 2010

(54) IMIDAZOLIDINE DERIVATIVES

(75) Inventors: Kazutaka Tachibana, Gotenba (JP); Haruhiko Sato, Gotenba (JP); Masateru Ohta, Gotenba (JP); Mitsuaki Nakamura, Gotenba (JP); Takuya Shiraishi, Gotenba (JP); Ikuhiro Imaoka, Gotenba (JP); Hitoshi Yoshino, Gotenba (JP); Masahiro Nagamuta, Tokyo (JP); Hiromitsu Kawata, Kamakura (JP)

(73) Assignee: Chugai Seiyaku Kabushiki Kaisha, Tokyo (JP)

( * ) Notice: Subject to any disclaimer, the term of this patent is extended or adjusted under 35 U.S.C. 154(b) by 714 days.

This patent is subject to a terminal disclaimer.

(21) Appl. No.: 11/659,369

(22) PCT Filed: Aug. 3, 2005

(86) PCT No.: PCT/JP2005/014195

§ 371 (c)(1), (2), (4) Date: Feb. 5, 2007

(87) PCT Pub. No.: WO2006/013887

PCT Pub. Date: Feb. 9, 2006

(65) Prior Publication Data

US 2007/0249697 A1    Oct. 25, 2007

(30) Foreign Application Priority Data

Aug. 3, 2004   (JP) ............................. 2004-227321

(51) Int. Cl.
A61K 31/4166  (2006.01)
C07D 233/40   (2006.01)

(52) U.S. Cl. ................. 514/389; 548/316.4; 548/317.1; 548/319.1; 514/385; 514/386

(58) Field of Classification Search ............. 548/316.4, 548/317.1, 319.1; 514/385, 386, 389
See application file for complete search history.

(56) References Cited

U.S. PATENT DOCUMENTS 5,411,981 A    5/1995  Gaillard-Kelly et al.
5,627,201 A    5/1997  Gaillard-Kelly et al.
7,271,188 B2 * 9/2007  Tachibana et al. ........... 514/391
2006/0135583 A1 6/2006  Tachibana et al.

FOREIGN PATENT DOCUMENTS

| JP | 6-73017 A | 3/1994 |
|---|---|---|
| WO | WO 97/00071 A1 | 1/1997 |
| WO | 2004/111012 A1 | 12/2004 |
| WO | WO 2004/011012 A1 | 12/2004 |

* cited by examiner

Primary Examiner—Golam M Shameem
(74) Attorney, Agent, or Firm—Browdy and Neimark, PLLC

(57) ABSTRACT

The present invention provides a compound represented by formula (I):

$$Q-N \underset{X^2}{\overset{X^1}{\underset{\|}{\bigcirc}}} \underset{Me}{\overset{Me}{\bigcirc}} (CH_2)_n-SO_2-N \underset{R^2}{\overset{R^1}{}}$$

wherein n is an integer selected from 1 to 20, Q is

[structures with (E)$_m$, A, B substituents on phenyl or naphthyl rings]

A is cyano or the like; B is hydrogen, halogen, or the like; $X^1$ and $X^2$ are each independently selected from O and S; E is a $C_{1-4}$ alkyl group; and $R^1$, $R^2$, $R^3$ and $R^4$ are each independently selected from a hydrogen atom and a $C_1$-$C_6$ alkyl group, and a drug, a pharmaceutical composition containing the compound, and the like.

12 Claims, No Drawings

IMIDAZOLIDINE DERIVATIVES

FIELD OF THE INVENTION

The present invention relates to imidazolidine derivatives which have a substituted alkyl group in 3-position, and a drug containing these imidazolidine derivatives as a active ingredient.

BACKGROUND ART

It has been made clear in the past that the male hormone androgen plays an important role in prostate cancer, benign prostatic hypertrophy, male pattern baldness, sexual precociousness, common acne, seborrhea and hypertrichosis. For example, it is known that persons who have been castrated and persons suffering from sexual gland failure almost never develop prostate cancer or benign prostatic hypertrophy.

For example, cyproterone acetate, chlormadinone acetate, flutamide, bicalutamide and the like are used as anti-androgen agents, i.e., androgen receptor antagonists. These anti-androgen agents show an effect in many cases such as drug therapy in prostate cancer, and constitute important treatment drugs in this area. Furthermore, it is known that cyproterone acetate suppresses the occurrence of baldness and the progression of acne in teenagers. Furthermore, in females, cyproterone acetate is used in the treatment of androgenization and hair loss. Flutamide and bicalutamide are used as prostate cancer treatment agents.

However, as problems encountered in these anti-androgen agents, it is known that even if the anti-androgen agents are effective, the disorder recurs in almost all cases in two to five years, and in such cases, androgen resistance appears.

Furthermore, it has been reported that hydroxyflutamide, which is the active form of flutamide, causes an increase in androgen receptor transcription activity at a concentration of 10 µmol/L. Moreover, the hydroxyflutamide concentration in the blood in prostate cancer patients treated with flutamide is several µmol/L. However, it has been reported that this concentration reaches a concentration at which hydroxyflutamide shows an agonist effect (see Non-patent Document 1).

Furthermore, it has been reported that there is an increase in the weight of the prostate gland when cyproterone acetate and chlormadinone acetate are continuously administered to castrated rats for two weeks (see Non-patent Document 2). Moreover, in regard to flutamide and bicalutamide, there are also reports of side effects such as liver toxicity and the like. Accordingly, there is a demand for an anti-androgen agent which has a sufficient antagonistic effect, and in which these problems have been solved.

Meanwhile, the compounds represented by the following formula described in Japanese Patent Application No. 4-308579 A (Patent Document 1) and the corresponding European Patent Application No 494819 A (Patent Document 2) are known as phenylimidazolidines that show anti-androgen activity.

[Formula 1]

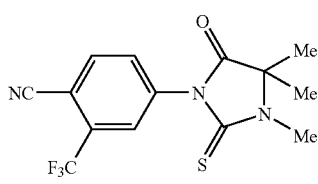

Furthermore, the compounds represented by the following formula described in Japanese Patent Application No. 10-510845 A (Patent Document 3) and the corresponding International Patent Publication WO 97/00071 (Patent Document 4) are known as substituted phenylimidazolidiens that show anti-androgen activity.

[Formula 2]

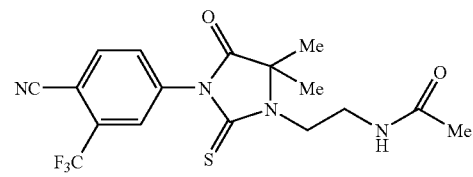

However, the compounds likewise do not constitute means for solving the problems of existing anti-androgen agents.

[Patent Document 1]
  Japanese Patent Application No. 4-308579 A
[Patent Document 2]
  European Patent Application No 494819 A
[Patent Document 3]
  Japanese Patent Application No. 10-510845 A
[Patent Document 4]
  International Patent Publication WO 97/00071
[Non-patent Document 1]
  J. Biol. Chem., Vol. 270, pp. 19998-20003, 1995
[Non-patent Document 2]
  Journal of the Endocrine Society of Japan, Vol. 66, pp. 597-606, 1990

DISCLOSURE OF THE INVENTION

Problems to be Solved by the Invention

It is one object of the present invention to provide imidazolidine derivatives which have a substituted alkyl group in 3-position, and which show a useful activity as drugs, especially an anti-androgen activity, and pharmaceutically acceptable salts, prodrugs or solvates thereof.

It is another object of the present invention to provide drugs containing the abovementioned imidazolidine derivatives.

Means to Solve the Problem

The present inventors conducted diligent research with the aim of solving the abovementioned problems. As a result of this research, the inventors found that imidazolidine derivatives having a sulfonamide group represented by Formula (I) show anti-androgen activity, and show no or almost no agonist activity, and then completed the present invention.

Specifically, according to one aspect of the present invention, there provides a compound represented by formula (I):

[Formula 3]

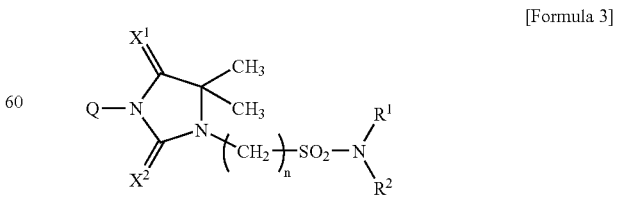

(I)

wherein, n is an integer selected from 1 to 20, Q is

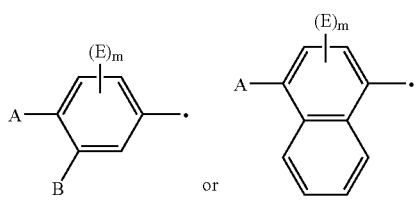

[Formula 4]

A is cyano group, —COOR³, —CONR³R⁴, a $C_1$-$C_4$ alkyl group which may be substituted by one or more halogen atoms, or a nitro group;

B is a hydrogen atom, a halogen atom, —OR³ or a $C_1$-$C_4$ alkyl group which may be substituted by one or more halogen atoms;

$X^1$ and $X^2$ are independently selected from O and S;

m is an integer selected from 0 to 3;

E is independently a $C_1$-$C_4$ alkyl group;

$R^1$ and $R^2$ are independently selected from a hydrogen atom, a $C_1$-$C_6$ alkyl group, and a $C_1$-$C_6$ alkylcarbonyl group;

$R^3$ and $R^4$ are independently selected from a hydrogen atom and a $C_1$-$C_6$ alkyl group;

with the proviso that when $X^1$ is O and $X^2$ is S, Q is not 4-cyano-3-trifluoromethylphenyl group, or a pharmaceutically acceptable salt, a prodrug or a solvate thereof.

Here, it is preferable that A is trifluoromethyl group, cyano group, carboxy group, carbamoyl group, N-methylcarbamoyl group, N,N-dimethylcarbamoyl group, or nitro group. Furthermore, it is preferable that B is a hydrogen atom, trifluoromethyl group, methyl group, ethyl group, a chlorine atom, or methoxy group. Moreover, a case in which $X^1$ is O, and $X^2$ is O or S is preferable. Furthermore, n is preferably an integer selected from 1 to 10.

In the abovementioned Formula (I), for example, a case in which $R^1$ and $R^2$ are both hydrogen atoms, or a case in which one of these is a methyl group, is preferable. Furthermore, $R^3$ and $R^4$ defined in the abovementioned Formula (I) are preferably independently selected from a hydrogen atoms and methyl group.

Examples of suitable compounds represented by the abovementioned Formula (I) include the following:

3-[3-(3-chloro-4-cyanophenyl)-5,5-dimethyl-4-oxo-2-thioxoimidazolidin-1-yl]propane-1-sulfonic acid amide;
3-[3-(4-cyano-3-methoxyphenyl)-5,5-dimethyl-4-oxo-2-thioxoimidazolidin-1-yl]propane-1-sulfonic acid amide;
3-[3-(4-cyano-2-methyl-3-trifluoromethylphenyl)-5,5-dimethyl-4-oxo-2-thioxoimidazolidin-1-yl]propane-1-sulfonic acid amide;
3-[3-(4-cyano-2-methyl-5-trifluoromethylphenyl)-5,5-dimethyl-4-oxo-2-thioxoimidazolidin-1-yl]propane-1-sulfonic acid amide;
3-[3-(4-nitro-3-trifluoromethylphenyl)-5,5-dimethyl-4-oxo-2-thioxoimidazolidin-1-yl]propane-1-sulfonic acid amide;
3-[3-(4-cyano-3-methylphenyl)-5,5-dimethyl-4-oxo-2-thioxoimidazolidin-1-yl]propane-1-sulfonic acid amide;
3-[3-(4-cyano-3-ethylphenyl)-5,5-dimethyl-4-oxo-2-thioxoimidazolidin-1-yl]propane-1-sulfonic acid amide;
3-[3-(3-methyl-4-nitrophenyl)-5,5-dimethyl-4-oxo-2-thioxoimidazolidin-1-yl]propane-1-sulfonic acid amide;
3-[3-(4-trifluoromethylnaphth-1-yl)-5,5-dimethyl-4-oxo-2-thioxoimidazolidin-1-yl]propane-1-sulfonic acid amide;
3-[3-(4-cyanophenyl)-5,5-dimethyl-4-oxo-2-thioxoimidazolidin-1-yl]propane-1-sulfonic acid amide;
3-[3-(4-carboxyphenyl)-5,5-dimethyl-4-oxo-2-thioxoimidazolidin-1-yl]propane-1-sulfonic acid amide;
3-[3-(4-aminocarbonylphenyl)-5,5-dimethyl-4-oxo-2-thioxoimidazolidin-1-yl]propane-1-sulfonic acid amide;
3-[3-{4-(N,N-dimethylaminocarbonyl)phenyl}-5,5-dimethyl-4-oxo-2-thioxoimidazolidin-1-yl]propane-1-sulfonic acid amide;
3-[3-(4-carboxy-3-trifluoromethylphenyl)-5,5-dimethyl-4-oxo-2-thioxoimidazolidin-1-yl]propane-1-sulfonic acid amide;
3-[3-(4-aminocarbonyl-3-trifluoromethylphenyl)-5,5-dimethyl-4-oxo-2-thioxoimidazolidin-1-yl]propane-1-sulfonic acid amide;
3-[3-{4-(N,N-dimethylaminocarbonyl)-3-trifluoromethylphenyl}-5,5-dimethyl-4-oxo-2-thioxoimidazolidin-1-yl]propane-1-sulfonic acid amide;
3-[3-(4-cyanonaphth-1-yl)-5,5-dimethyl-4-oxo-2-thioxoimidazolidin-1-yl]propane-1-sulfonic acid amide;
3-[3-(4-nitronaphth-1-yl)-5,5-dimethyl-4-oxo-2-thioxoimidazolidin-1-yl]propane-1-sulfonic acid amide;
3-[3-(4-aminocarbonylnaphth-1-yl)-5,5-dimethyl-4-oxo-2-thioxoimidazolidin-1-yl]propane-1-sulfonic acid amide;
3-[3-(4-(N,N-dimethylaminocarbonyl)naphth-1-yl)-5,5-dimethyl-4-oxo-2-thioxoimidazolidin-1-yl]propane-1-sulfonic acid amide;
3-[3-(3-chloro-4-cyanophenyl)-5,5-dimethyl-2,4-dioxoimidazolidin-1-yl]propane-1-sulfonic acid amide;
3-[3-(4-cyano-3-methoxyphenyl)-5,5-dimethyl-2,4-dioxoimidazolidin-1-yl]propane-1-sulfonic acid amide;
3-[3-(4-cyano-2-methyl-3-trifluoromethylphenyl)-5,5-dimethyl-2,4-dioxoimidazolidin-1-yl]propane-1-sulfonic acid amide;
3-[3-(4-cyano-2-methyl-5-trifluoromethylphenyl)-5,5-dimethyl-2,4-dioxoimidazolidin-1-yl]propane-1-sulfonic acid amide;
N-methyl-3-[3-(3-chloro-4-cyanophenyl)-5,5-dimethyl-4-oxo-2-thioxoimidazolidin-1-yl]propane-1-sulfonic acid amide;
4-[3-(3-chloro-4-cyanophenyl)-5,5-dimethyl-4-oxo-2-thioxoimidazolidin-1-yl]butane-1-sulfonic acid amide;
5-[3-(3-chloro-4-cyanophenyl)-5,5-dimethyl-4-oxo-2-thioxoimidazolidin-1-yl]pentane-1-sulfonic acid amide;
2-[3-(3-chloro-4-cyanophenyl)-5,5-dimethyl-4-oxo-2-thioxoimidazolidin-1-yl]ethane-1-sulfonic acid amide;
2-[3-(3-chloro-4-cyanophenyl)-5,5-dimethyl-2,4-dioxoimidazolidin-1-yl]ethane-1-sulfonic acid amide; and
N-acetyl-3-[3-(3-chloro-4-cyanophenyl)-5,5-dimethyl-4-oxo-2-thioxoimidazolidin-1-yl]propane-1-sulfonic acid amide.

According to another aspect of the present invention, there provides drugs, pharmaceutical compositions and anti-androgen agents containing compounds represented by the abovementioned Formula (I), or pharmaceutically acceptable salts, prodrugs or solvates of these compounds, as active ingredients.

According to still another aspect of the present invention, there provides prophylactic or therapeutic agents for disorders selected from prostate cancer, benign prostatic hypertrophy, male pattern baldness, sexual precociousness, common acne, seborrhea and hypertrichosis, which contains compounds represented by the abovementioned Formula (I), or pharmaceutically acceptable salts, prodrugs or solvates of these compounds, as active ingredients.

According to still another aspect of the present invention, there provides the use of the above-mentioned compounds represented by the abovementioned Formula (I), or pharmaceutically acceptable salts, prodrugs or solvates of these compounds, in manufacturing medicaments that act as androgen receptor antagonists.

According to still another aspect of the present invention, there provides a process for preparing a compound represented by formula (I):

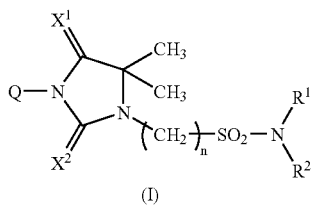

[Formula 5]

wherein, Q, $X^1$, $X^2$, n, $R^1$ and $R^2$ are as described hereinbefore, comprising steps of:

reacting a compound represented by formula (II):

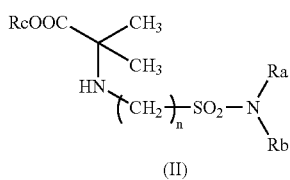

[Formula 6]

wherein n is an integer selected from integers of 1 to 20;

Ra and Rb are each independently selected from a $C_1$-$C_6$ alkyl group substituted by one or more $W^1$, a $C_1$-$C_6$ alkylcarbonyl group which may be substituted by one or more $W^1$, an arylcarbonyl group which may be substituted by one or more $W^2$, a $C_1$-$C_6$ alkoxycarbonyl group which may be substituted by one or more $W^1$, an aryloxycarbonyl group which may be substituted by one or more $W^2$, a $C_1$-$C_6$ alkylaminocarbonyl group which may be substituted by one or more $W^1$, a di($C_1$-$C_6$ alkyl)aminocarbonyl group which may be substituted by one or more $W^1$, a $C_1$-$C_6$ alkylsulfonyl group which may be substituted by one or more $W^1$, and an arylsulfonyl group which may be substituted by one or more $W^2$, and $R^1$ and $R^2$; or Ra and Rb may be joined together to form a group =CH—$W^3$;

$W^1$ is a $C_1$-$C_6$ alkoxy group, a $C_1$-$C_6$ alkylthio group, a $C_1$-$C_6$ alkylsulfynyl group, a $C_1$-$C_6$ alkylsulfonyl group, an aryl group which may be substituted by one or more $W^2$, an aryloxy group which may be substituted by one or more $W^2$, or a $C_7$-$C_{14}$ aralkyloxy group which may be substituted by one or more $W^2$;

$W^2$ is a $C_1$-$C_6$ alkyl group, a $C_1$-$C_6$ alkoxy group, a $C_1$-$C_6$ haloalkyl group, a halogen atom, cyano group, or nitro group;

$W^3$ is a $C_1$-$C_6$ alkyl group, a $C_1$-$C_6$ alkoxy group, a $C_1$-$C_6$ alkylamino group, a di($C_1$-$C_6$ alkyl)amino group;

$R^1$ and $R^2$ are as defined hereinbefore; and

Rc is a $C_1$-$C_6$ alkyl group, with a compound represented by the following formula (IV):

Q-N=C=$X^2$    (IV)

wherein, Q and $X^2$ are as defined hereinbefore, to obtain a compound represented by formula (III):

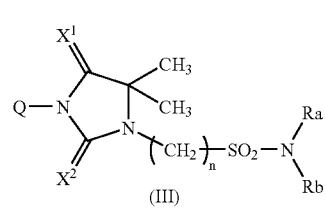

[Formula 7]

wherein, Q, $X^1$, $X^2$, n, Ra and Rb are as described hereinbefore; and a deprotection in cases where at least one of the groups Ra and Rb is other than $R^1$ and $R^2$.

Furthermore, according to another aspect of the present invention, there also provides a compound represented by Formula (II):

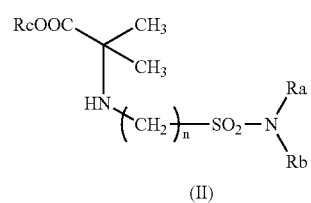

[Formula 8]

wherein n, Ra, Rb and Rc are as defined hereinbefore, and a compound represented by Formula (III):

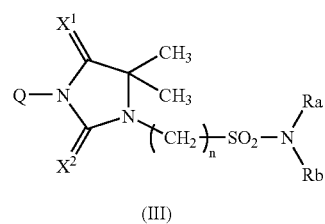

[Formula 9]

wherein Q, $X^1$, $X^2$, n, Ra, and Rb are as defined hereinbefore.

In the present invention, the following terms include the meanings described below unless specifically noted otherwise.

The term $C_1$-$C_6$ alkyl group refers to a linear or branched alkyl group with 1 to 6 carbon atoms. Examples of such a group include methyl group, ethyl group, n-propyl group, i-propyl group, n-butyl group, s-butyl group, i-butyl group, t-butyl group, n-pentyl group, 3-methylbutyl group, 2-methylbutyl group, 1-methylbutyl group, 1-ethylpropyl group, n-hexyl group and the like. A linear or branched alkyl group with 1 to 3 carbon atoms is preferable, and methyl group is more preferable, as $R^1$ or $R^2$ in Formula (I) of the present invention.

The term $C_1$-$C_4$alkyl group refers to a linear or branched alkyl group with 1 to 4 carbon atoms. Examples of such a group include methyl group, ethyl group, n-propyl group, i-propyl group, n-butyl group, s-butyl group, i-butyl group, t-butyl group and the like.

The term $C_1$-$C_6$ alkoxy group refers to a linear or branched alkoxy group of 1 to 6 carbon atoms which has an alkyl group defined above as the alkyl moiety. Examples of $C_1$-$C_6$ alkoxy group include methoxy group, ethoxy group, n-propoxy group, i-propoxy group, n-butoxy group, s-butoxy group, i-butoxy group, t-butoxy group, n-pentoxy group, 3-methyl-butoxy group, 2-methylbutoxy group, 1-methylbutoxy group, 1-ethylpropoxy and n-hexyloxy group.

The term $C_1$-$C_6$ alkylcarbnonyl group refers to a linear or branched alkylcarbonyl group with 1 to 6 carbon atoms having an alkyl group defined above as the alkyl moiety. Examples of $C_1$-$C_6$ alkylcarbonyl group include acetyl group, propionyl group, 2-methylpropionyl group, 2,2-dimethylpropionyl group and the like.

The term aryl group refers to a single-ring or fused-ring aromatic hydrocarbon group with 6 to 14 carbon atoms. Examples of such a group include phenyl group, 1-naphthyl group, 2-naphthyl group, anthracenyl group and the like. Furthermore, the same is true in cases where an aryl group is included as parts of other substituents.

An aryloxy group is a group that has the already-defined aryl as aryl moieties. Examples include phenoxy group, 1-naphthyloxy group, 2-naphthyloxy group and the like.

Examples of arylcarbonyl group include benzoyl group, 1-naphthoyl group, 2-naphthoyl group and the like.

A $C_1$-$C_6$ alkoxylcarbonyl group refers to a linear or branched alkoxycarbonyl group with 1 to 6 carbon atoms. This group has the already-defined alkyl group as alkyl moieties. Examples of a $C_1$-$C_6$ alkoxylcarbonyl group include methoxycarbonyl group, ethoxycarbonyl group, t-butoxycarbonyl group and the like.

Examples of aryloxycarbonyl group include phenoxycarbonyl group, 1-naphthyloxycarbonyl group, 2-naphthyloxy carbonyl group and the like.

A $C_1$-$C_6$ alkylaminocarbonyl group refers to a linear or branched alkylaminocarbonyl group of 1 to 6 carbon atoms, which has the already-defined alkyl group as alkyl moieties. Examples of $C_1$-$C_6$ alkylaminocarbonyl group include methylaminocarbonyl group, ethylaminocarbonyl group, t-butylaminocarbonyl group and the like.

A di($C_1$-$C_6$ alkyl)aminocarbonyl group refers to a linear or branched dialkylaminocarbonyl group with 1 to 6 carbon atoms which has the already-defined alkyl group as alkyl moieties. Examples of di($C_1$-$C_6$ alkyl)aminocarbonyl group include dimethylaminocarbonyl group, diethylaminocarbonyl group diisopropylaminocarbonyl group, methyl-t-butylaminocarbonyl group and the like.

A $C_1$-$C_6$ alkylthio group refers to a linear or branched alkylthio group with 1 to 6 carbon atoms, which have the already-defined alkyl group as alkyl moieties. Examples of $C_1$-$C_6$ alkylthio group include methylthio group, ethylthio group and the like.

A $C_1$-$C_6$ alkylsulfynyl group refer to a linear or branched alkylsulfynyl group with 1 to 6 carbon atoms, which has the already-defined alkyl group as alkyl moieties. Examples of $C_1$-$C_6$ alkylsulfynyl group include methylsulfynyl group, ethylsulfynyl group and the like.

A $C_1$-$C_6$ alkylsulfonyl group refers to a linear or branched alkylsulfonyl group with 1 to 6 carbon atoms, which has the already-defined alkyl group as alkyl moieties. Examples of such alkylsulfonyl group include methanesulfonyl group, ethanesulfonyl group and the like.

Examples of an arylsulfonyl group include benzenesulfonyl group, 1-naphthalenesulfonyl group, 2-naphthalenesulfonyl group and the like.

A $C_7$-$C_{14}$ aralkyl group refers to an aralkyl group with 7 to 14 carbon atoms which has a linear or branched alkyl moiety with 1 to 8 carbon atoms. Examples of such group include benzyl group, 1-phenethyl group, 2-phenethyl group and the like.

A $C_7$-$C_{14}$ aralkyloxy group refers to an aralkyloxy group with a total of 7 to 14 carbon atoms which has a linear or branched alkyl moiety with 1 to 8 carbon atoms. Examples of such a group include benzyloxy group, 1-phenethyloxy group, 2-phenethyloxy group and the like.

Halogen atoms refer to fluorine atoms, chlorine atoms, bromine atoms, iodine atoms and the like.

A $C_1$-$C_4$ alkyl group that may be substituted by one or more halogen atoms includes a $C_1$-$C_4$ alkyl group and a $C_1$-$C_4$ haloalkyl group.

A $C_1$-$C_4$ haloalkyl group refers to a linear or branched alkyl group with 1 to 4 carbon atoms substituted by one or more of the halogen atoms defined above, which has the already-defined alkyl group as a linear or branched alkyl moiety with 1 to 4 carbon atoms. Examples of such a haloalkyl group include fluoromethyl group, chloromethyl group, bromomethyl group, difluoromethyl group, trifluoromethyl group, dichloromethyl group, trichloromethyl group, chlorodifluoromethyl group, 1,1,1-trifluoroethyl group, 1,1,1-trichloroethyl group, perfluoroethyl group, perfluoropropyl group and the like.

A $C_1$-$C_6$ haloalkyl group refers to a linear or branched alkyl group with 1 to 6 carbon atoms substituted by one or more of the halogen atoms defined above, which has the already-defined alkyl group as a linear or branched alkyl moiety with 1 to 6 carbon atoms. Examples of such a haloalkyl group include a $C_1$-$C_6$ haloalkyl group defined above.

In addition to the abovementioned substituent group, examples of Ra and Rb include a $C_1$-$C_6$ alkoxy $C_1$-$C_6$ alkyl group such as methoxymethyl group, ethoxymethyl group, methoxyethyl group and the like; a $C_7$-$C_{14}$ aralkyloxy $C_1$-$C_6$ alkyl group such as benzyloxymethyl group and the like; a $C_7$-$C_{14}$ aralkyl group such as benzyl group, 4-methoxybenzyl group and the like; a $C_7$-$C_{14}$ aralkyloxycarbonyl group such as benzyloxy carbonyl group and the like; p-toluenesulfonyl group, and the like.

Examples of the abovementioned group =CH—$W^3$ include the group =CH—$CH_3$, the group =CH—$N(CH_3)_2$, the group =CH—$N(CH_2CH_3)_2$, the group =CH—$OCH_3$, the group =CH—$OCH_2CH_3$ and the like. These groups may be cis forms, trans forms or a mixture thereof.

Q is preferably a group represented by the following formula:

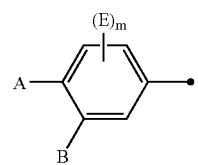

[Formula 10]

wherein A, B and E represent the same meanings as A, B and E defined in the specification.

Here, A is preferably cyano group, —$CONR^3R^4$ or nitro group, and is even more preferably cyano group or nitro group.

In the abovementioned formula, B is preferably trifluoromethyl group, a halogen atom, —$OR^3$ or a $C_1$-$C_4$ alkyl group, and is even more preferably trifluoromethyl group, a halogen atom or —$OR^3$.

$R^3$ and $R^4$ may be the same or different, and are preferably a hydrogen atom, or a linear or branched alkyl group with 1 to 3 carbon atoms, and are even more preferably a hydrogen atom, methyl group or ethyl group.

m is preferably 0 or 1, and E is preferably methyl group.

$X^1$ and $X^2$ may be the same or different, and are O or S. Preferably, $X^1$ is O, and $X^2$ is O or S. However, in cases where $X^1$ is O and $X^2$ is S, Q is not 4-cyano-3-trifluoromethylphenyl group.

Preferably, n is 1, 2, 3, 4, 5, 6, 7, 8, 9 or 10, more preferably 2 to 9, and even more preferably 2 to 6. Furthermore, in cases where n is 3 or 4, a significant separation of agonist activity and antagonist activity is recognized in the compound of the present invention.

There are no particular restrictions on the deprotection process. However, examples of such processes include hydrolysis reactions performed in the presence of an acid or base, reduction reactions including hydrogenation using Pd/C or the like, dehydrogenation reactions using dichlorodicyanoquinone or the like, and other such reactions.

$R^1$ and $R^2$ may be the same or different, and these groups are preferably a hydrogen atom, a linear or branched alkyl group with 1 to 3 carbon atoms (a $C_1$-$C_3$ alkyl group), or a linear or branched alkylcarbonyl group with 1 to 3 carbon atoms (a $C_1$-$C_3$ alkylcarbonyl group).

Pharmaceutically acceptable salts of the compounds represented by formula (I) are salts which can be used as drugs, and which are manufactured by contacting the abovementioned compounds with acids or bases that can be used in the manufacture of drugs. Examples of such salts include hydrochloric acid salts, hydrobromic acid salts, hydroiodic acid salts, sulfuric acid salts, sulfonic acid salts, phosphoric acid salts, phosphonic acid salts, carboxylic acid salts such as acetic acid salts, citric acid salts, malic acid salts, salicylic acid salts and the like; or alkali metal salts such as sodium salts, potassium salts and the like, alkaline earth metal salts such as magnesium salts, calcium salts and the like, ammonium salts such as ammonium salts, alkylammonium salts, dialkylammonium salts, trialkylammonium salts, tetraalkylammonium salts and the like, and other such salts.

The term "a prodrug of a compound represented by formula (I)" includes a chemically modified compound that is designed to produce a compound represented by formula (I) in the body after being administered as drugs, by chemical reactions that take place in the body. Examples of such a prodrug include a compound obtained by a subjecting compound represented by formula (I) to a $C_1$-$C_6$ alkylcarbonyl conversion, $C_6$-$C_{10}$ arylcarbonyl conversion, $C_1$-$C_6$ alkoxycarbonyl conversion, $C_1$-$C_6$ alkylaminocarbonyl conversion, $C_1$-$C_6$ alkylsulfonyl conversion or the like, and a compound subjected to an imino conversion using a reagent such as N,N-dimethylformamide dimethylacetal or the like. Specific examples of a prodrug also include the compound represented by formula (III).

A solvate of a compound represented by formula (I) include a compound in which a molecule of a solvent that can be used in the manufacture of drugs is coordinated with the abovementioned compound. For example, such a solvate includes a hydrate.

The compound of the present invention represented by general formula (I) is expected to act as anti-androgen agents that do not show any appearance of androgen resistance due to long-term administration, and/or side effects such as toxicity or the like, and are expected to be useful as therapeutic agents for the treatment of disorders such as prostate cancer, benign prostatic hypertrophy, male pattern baldness, sexual precociousness, common acne, seborrhea and hypertrichosis. Furthermore, if the compounds of the present invention represented by general formula (I) are administered beforehand, it is expected that the onset of disorders such as prostate cancer, benign prostatic hypertrophy, male pattern baldness, sexual precociousness, common acne, seborrhea and hypertrichosis will be prevented or delayed. Accordingly, it is expected that these compounds will also constitute prophylactic agents for such disorders.

The pharmaceutical composition of the present invention contains a compound represented by formula (I), or a salt, a prodrug or a solvate thereof, in amounts that is effective in treatment, and a pharmaceutically acceptable carrier. If necessary, this composition may contain other chemotherapeutic agents. For example, one or more agents selected from cell division inhibiting agents, alkylating agents, metabolism inhibiting agents, intercalating antibiotics, growth factor inhibiting agents, cell period inhibiting agents, enzymes, enzyme inhibitors, aromatase inhibitors, topoisomerase inhibitors, biological response modifiers, anti-hormone agents, anti-estrogen agents and anti-androgen agents.

The compound of the present invention represented by general formula (I), as well as a salt, a prodrug and a solvate thereof, can be administered orally or non-orally in the form of pharmaceutical compositions which also contain pharmaceutically acceptable additive agents such as carriers, excipients, binders, diluents, stabilizing agents, lubricants, flavoring agents, disintegrating agents, coating agents, coloring agents, antioxidants, buffering agents, aqueous solvents, oily solvents, isotonic agents, dispersing agents, preservatives, solubilizing agents, fluidizing agents, analgesic agents, pH adjusting agents, antiseptic agents, base agents and the like. Examples of the abovementioned pharmaceutical composition include granules, powder, tablets, hard capsules, soft capsules, syrups, emulsions, suspensions and the like as orally administered agents. Examples of parenteral agents include injection agents such as subcutaneous injection agents, intravenous injection agents, intramuscular injection agents, intra-abdominal injection agents and the like; transdermal administration agents such as ointments, crèmes, lotions and the like; suppositories such as rectal suppositories, vaginal suppositories and the like; nasal administration formulations; and other agents. These formulations can be manufactured by publicly known methods that are commonly used in formulation processes.

Examples of excipients that can be used in the present invention include sugars such as lactose, white sugar, glucose, D-mannitol, sorbit and the like; cellulose and cellulose derivatives such as crystalline cellulose, hydroxypropylcellulose, hydroxypropylmethyl cellulose, methylcellulose and the like; starch and starch derivatives such as corn starch, potato starch, α-starch, dextrin, β-cyclodextrin, carboxymethylstarch sodium, hydroxypropylstarch and the like; silicates such as synthetic aluminum silicate, magnesium aluminum silicate, calcium silicate, magnesium silicate and the like; phosphates such as calcium phosphate and the like; carbonates such as calcium carbonate and the like; sulfates such as calcium sulfate and the like; tartaric acid, potassium hydrogentartarate, magnesium hydroxide and the like.

Examples of binders that can be used include agar, stearyl alcohol, gelatin, traganth, polyvinyl alcohols, polyvinylpyrrolidones; cellulose and cellulose derivatives such as crystalline cellulose, hydroxypropylcellulose, hydroxypropylmethyl cellulose, methylcellulose and the like; starch and starch derivatives such as corn starch, potato starch, α-starch, dextrin, β-cyclodextrin, carboxymethylstarch sodium, hydroxypropylstarch and the like; sugars such as lactose, white sugar, glucose, D-mannitol, sorbit and the like; and other binders.

Examples of stabilizing agents that can be used include hardened oils, sesame oil, sodium chondroitin sulfate, dibutylhydroxytoluene, adipic acid, ascorbic acid, L-ascorbic acid stearic acid esters, sodium L-ascorbate, L-aspartic acid, sodium L-aspartate, acetyltryptophan sodium, acetanilide, aprotinin liquid, aminoethysulfonic acid, aminoacetic acid, DL-alanine, L-alanine; para-oxybenzoic acid esters such as methylparaben, propylparaben and the like; alcohols such as chlorobutanol, benzyl alcohol, phenylethyl alcohol and the like; benzalkonium chloride; phenols such as phenol, cresol and the like; sorbic acid; sulfites such as sodium hydrogensulfite, sodium sulfite and the like; edetates such as sodium edetate, tetrasodium edetate and the like; and other stabilizing agents.

Examples of lubricants that can be used include powdered gum Arabic, cacao butter, carmellose calcium, carmellose sodium, caropeptide, hydrated silicon dioxide, hydrated amorphous silicon oxide, dry aluminum hydroxide gel, glycerol, light liquid paraffin, crystalline cellulose, hardened oils, synthetic aluminum silicate, sesame oil, wheat starch, talc, macrogols, phosphoric acid; stearic acids such as stearic acid, calcium stearate, magnesium stearate and the like; waxes such as bleached beeswax, carnauba wax and the like; sulfates such as sodium sulfate and the like; silicates such as magnesium silicate, light amorphous silicic acid and the like; laurylsulfates such as sodium laurylsulfate and the like; and other lubricants.

Examples of flavoring agents that can be used include ascorbic acid, L-aspartic acid, sodium L-aspartate, magnesium L-aspartate, aspartame, hydrangea tea, hydrangea tea extract, powdered hydrangea tea, aminoethylsulfonic acid, aminoacetic acid, DL-alanine, saccharine sodium, dl-menthol, l-menthols; sugars such as lactose, white sugar, glucose, D-mannitol and the like; and other taste enhancing agents.

Examples of disintegrating agents that can be used include agar, gelatin, traganth, adipic acid, alginic acid, sodium alginate; cellulose and cellulose derivatives such as crystalline cellulose, hydroxypropylcellulose, hydroxypropylmethyl cellulose, methylcellulose and the like; carbonates such as calcium carbonate, sodium hydrogencarbonate, magnesium carbonate and the like; starch and starch derivatives such as corn starch, potato starch, α-starch, dextrin, β-cyclodextrin, carboxymethylstarch sodium, hydroxypropylstarch and the like; and other agents.

Examples of coating agents that can be used include shellac, polyvinylpyrrolidiones, polyethylene glycols, macrogols, methacrylic acid copolymers, liquid paraffin, Eudragit; cellulose derivatives such as cellulose acetate, hydroxypropylcellulose, cellulose acetate phthalate, hydroxypropylmethylcellulose and the like; and other coating agents.

Examples of coloring agents that can be used include indigo carmine, caramel, riboflavin and the like.

Examples of buffering agents that can be used include aminoacetic acid, L-arginine, benzoic acid, sodium benzoate, ammonium chloride, potassium chloride, sodium chloride, dry sodium sulfite, dry sodium carbonate, dilute hydrochloric acid, citric acid, calcium citrate, sodium citrate, disodium citrate, calcium gluconate, L-glutamic acid, sodium L-glutamate, creatinine, chlorobutanol, crystalline sodium dihydrogenphosphate, disodium succinate, acetic acid, potassium acetate, sodium acetate, tartaric acid, sodium hydrogencarbonate, sodium carbonate, triethanolamine, lactic acid, sodium lactate liquid, glacial acetic acid, boric acid, maleic acid, citric anhydride, anhydrous sodium citrate, anhydrous sodium acetate, anhydrous sodium carbonate, anhydrous sodium monohydrogenphosphate, anhydrous trisodium phosphate, anhydrous sodium dihydrogenphosphate, dl-malic acid, phosphoric acid, trisodium phosphate, sodium hydrogenphosphate, dipotassium phosphate, potassium dihydrogenphosphate, sodium dihydrogenphosphate, sodium dihydrogenphosphate monohydrate and the like.

Examples of aqueous solvents that can be used include distilled water, physiological saline, Ringer's solution and the like.

Examples of oily solvents that can be used include propylene glycol; vegetable oils such as olive oil, sesame oil, cottonseed oil, corn oil and the like; and other agents.

Examples of isotonic agents that can be used include potassium chloride, sodium chloride, glycerol, sodium bromide, D-sorbitol, nicotinic acid amide, glucose, boric acid and the like.

Examples of dispersing agents that can be used include gum arabic, alginic acid propylene glycol ester, sorbitan sesquioleate, D-sorbitol, traganth, methylcellulose, aluminum monostearate, aminoalkyl methacrylate copolymer RS, lactose, concentrated glycerol, propylene glycol, macrogols, sodium laurylsulfate; stearic acid and salts thereof such as zinc stearate, magnesium stearate and the like; and other dispersing agents.

Examples of preservatives that can be used include benzalkonium chloride, benzethonium chloride, dry sodium sulfite, dry sodium sulfate, cresol, chlorocresol, dibutylhydroxytoluene, potassium sorbate, sodium dehydroacetate, phenol, formalin, phosphoric acid, gum benzoin, thymerosal, thymol; alcohols such as chlorobutanol, phenethyl alcohol, propylene glycol, benzyl alcohol and the like; para-oxybenzoic acid esters such as isobutyl para-oxybenzoate, ethyl para-oxybenzoate, methyl para-oxybenzoate and the like; and other preservatives.

Examples of solubilizing agents that can be used include sodium benzoate, ethylenediamine, citric acid, sodium citrate, glycerol, sodium acetate, sodium salicylate, sorbitan sesquioleate, nicotinic acid amide, glucose, benzyl alcohol, polyvinylpyrrolidones, acetone, ethanol, isopropanol, D-sorbitol, sodium hydrogencarbonate, sodium carbonate, lactose, urea, white sugar and the like.

Examples of fluidizing agents that can be used include hydrated silicon dioxide, talc, anhydrous ethanol, crystalline cellulose, synthetic aluminum silicate, calcium hydrogenphosphate; stearic acid and salts of the same such as magnesium stearate and the like; and other agents.

Examples of analgesic agents that can be used include benzalkonium chloride, procaine hydrochloride, meprylcaine hydrochloride, lidocaine hydrochloride, lidocaine and the like.

Examples of pH adjusting agents that can be used include hydrochloric acid, citric acid, succinic acid, acetic acid, boric acid, maleic acid, sodium hydroxide and the like.

Examples of antiseptic agents that can be used include benzoic acid, sodium benzoate, cetylpyridinium chloride, salicylic acid, sodium salicylate, sorbic acid, potassium sorbate, thymol, methyl para-oxybenzoate, butyl para-oxybenzoate and the like.

Examples of base agents that can be used include glycerol, stearyl alcohol, polyethylene glycols, propylene glycol, cetanol, lard, white Vaseline, paraffin, bentonite, lanoline fatty acid isopropyl ester, Vaseline, polysorbates, macrogols, lauryl alcohol, sodium laurylsulfate, ethyl linolate, sodium hydrogenphosphate, rosin; vegetable oils such as olive oil, sesame oil, wheat germ oil and the like; and other base agents.

The amount of compounds represented by general formula (I) in the pharmaceutical composition of the present invention varies according to the dosage form, but is preferably approximately 0.1 to 100 wt % based on the total amount of the pharmaceutical composition. Furthermore, the amount of the pharmaceutical composition of the present invention that is administered may vary over a wide range depending on the subject of administration (warm-blooded animals such as humans), seriousness of the disorder, age, sex, administration method, physician's diagnosis and the like. However, in regard to the amount of compounds represented by formula (I) administered to adults, it is preferable that this amount be approximately 0.1 to 500 mg/kg per day both in the case of oral administration and in the case of parenteral administration. Furthermore, the abovementioned administration amount is the value per unit weight of the object of administration. Furthermore, in the present invention, depending on the seriousness of the disorder, judgment of the physician and the like, the abovementioned administration amount may be administered as one dose in a period ranging from one day to one month, or may be divided into several doses or more.

The compounds of the present invention can be manufactured by method A indicated below:

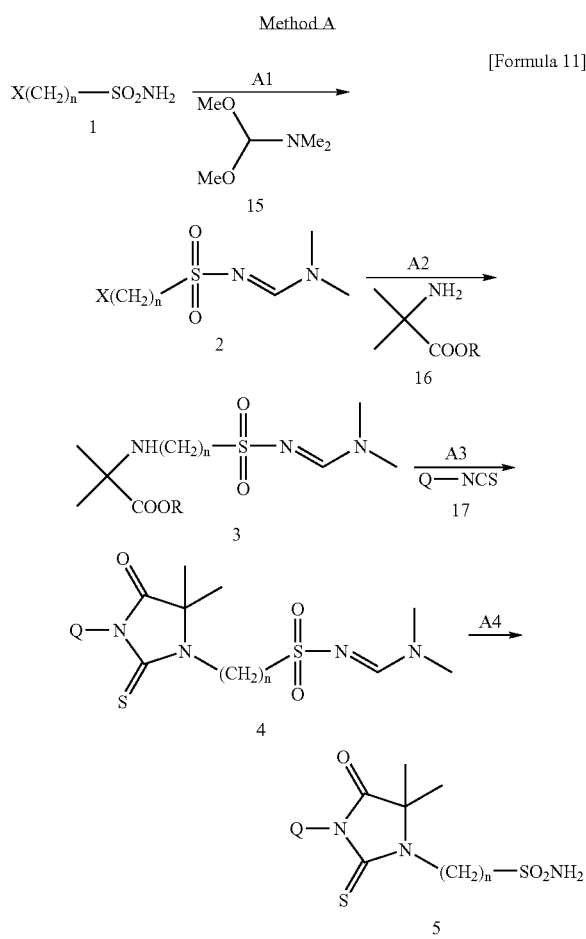

wherein, Q and n are as defined hereinbefore, R is a $C_1$-$C_6$ alkyl group, preferably a $C_1$-$C_3$ alkyl group, and even more preferably methyl group or ethyl group, and X is a halogen atom such as a chlorine atom, a bromine atom, an iodine atom or the like, or a leaving group such as methanesulfonyloxy group, p-toluenesulfonyloxy group or the like, and is preferably a halogen atom such as a chlorine atom, a bromine atom, an iodine atom or the like.

Method A is a method for preparing compound 5, in which both $R^1$ and $R^2$ are a hydrogen atom among the compounds represented by general formula (I).

Step A1 is a step in which compound 2 is manufactured; this compound is manufactured by reacting compound 1 and compound 15 in an inert solvent.

There are no particular restrictions on the inert solvent used, as long as this solvent does no participate in the reaction; examples of such inert solvents include halogen type solvents such as dichloromethane, chloroform and carbon tetrachloride, ether type solvents such as diethyl ether, tetrahydrofuran, dioxane and dimethoxyethane; ester type solvents such as ethyl acetate and methyl acetate; aromatic solvents such as benzene, toluene, xylene, quinoline and chlorobenzene; and also cyclohexane, dimethylsulfoxide, dimethylacetamide, dimethylimidazolidinone, dimethylformamide; N-methylpyrrolidone, acetonitrile and the like. Especially suitable are dimethylsulfoxide, dimethylacetamide, dimethylimidazolidinone, dimethylformamide, N-methylpyrrolidone, acetonitrile, ethyl acetate and the like, with dimethylformamide and the like being even more preferable. The reaction temperature varies depending on the type of solvent used and the like, but is ordinarily −30° C. to 100° C., and is preferably 0° C. to 50° C. The reaction time varies depending on the reaction temperature and the like, but is ordinarily 10 minutes to 48 hours, and is preferably 30 minutes to 24 hours.

Step A2 is a step in which compound 3 is manufactured; this is achieved by reacting compound 2 and compound 16 in the presence of a base with or without additives in an inert solvent.

There are no particular restrictions on the inert solvent used, as long as this solvent does not participate in the reaction; examples of such inert solvents include halogen type solvents such as dichloromethane, chloroform and carbon tetrachloride; ether type solvents such as diethyl ether, tetrahydrofuran, dioxane and dimethoxyethane; aromatic solvents such as benzene, toluene, xylene, quinoline and chlorobenzene; and also cyclohexane, dimethylsulfoxide, dimethylacetamide, dimethylimidazolidinone, dimethylformamide, N-methylpyrrolidone, acetonitrile and the like. Especially suitable are dimethylsulfoxide, dimethylacetamide, dimethylimidazolidinone, dimethylformamide, N-methylpyrrolidone, acetonitrile and the like. These inert solvents may be used singly or in mixtures.

Examples of bases that can be used include carbonates such as potassium carbonate, sodium carbonate and cesium carbonate; metal hydrides such as sodium hydride, potassium hydride and calcium hydride; alkyllithium compounds such as methyllithium, ethyllithium, n-butyllithium and t-butyllithium; metal hydroxides such as lithium hydroxide, sodium hydroxide, potassium hydroxide, calcium hydroxide, barium hydroxide and cesium hydroxide; metal amides such as sodium amide, potassium bistrimethylsilylamide, sodium bistrimethylsilylamide and lithium diisoprylamide; amines such as triethylamine, diisopropylethylamine, 1,8-diazabicyclo[5.4.0]-7-undecene, pyridine, dimethylaminopyridine and pyrazine; and other compounds such as sodium tetraborate, sodium iodide, lithium hexamethyldisilazane, sodium hexamethyldisilazane, potassium hexamethyldisilazane and the like. Especially suitable are carbonates such as potassium carbonate and sodium carbonate.

There are no particular restrictions on additives used, as long as these additive accelerate the progress of the reaction; examples of additives that can be used include potassium iodide, sodium iodide, tetra-n-butylammonium iodide and the like.

The reaction temperature varies according to the type of solvent used and the like, but is ordinarily 0° C. to 150° C. and is preferably 30° C. to 100° C. The reaction time varies according to the reaction temperature and the like, but is ordinarily 10 minutes to 48 hours, and is preferably 30 minutes to 24 hours.

Step A3 is a step in which compound 4 is manufactured; this is achieved by reacting compound 3 and compound 17 in the presence of a base or without a base in an inert solvent.

There are no particular restrictions on the inert solvent used, as long as this solvent does not participate in the reaction. However, examples of such inert solvents include halogen type solvents such as dichloromethane, chloroform and carbon tetrachloride; ether type solvents such as diethyl ether, tetrahydrofuran, dioxane and dimethoxyethane; aromatic solvents such as benzene, toluene, xylene, quinoline and chlorobenzene, and also cyclohexane, dimethylsulfoxide, dimethylacetamide, dimethylimidazolidinone, dimethylformamide, N-methylpyrrolidone, acetonitrile and the like. Especially suitable are halogen type solvents such as dichloromethane, chloroform and carbon tetrachloride, and ether type solvents such as diethyl ether, tetrahydrofuran, dioxane and dimethoxyethane, and dichloromethane, tetrahydrofuran and the like are even more preferable.

Examples of bases that can be used include amines such as triethylamine, diisopropylethylamine, 1,8-diazabicyclo[5.4.0]-7-undecene, pyridine, dimethylaminopyridine and pyrazine. Preferably, the base used is triethylamine, dimethylaminopyridine or the like. Such a base may be used or omitted. However, the use of a base is preferable.

The reaction temperature varies according to the type of solvent used and the like, but is ordinarily −30° C. to 100° C., and is preferably 0° C. to 50° C. The reaction time varies depending on the reaction temperature and the like, but is ordinarily 10 minutes to 48 hours, and is preferably 30 minutes to 24 hours.

Step A4 is a step in which compound 5 is manufactured; this is achieved by hydrolyzing compound 4 in an inert solvent.

There are no particular restrictions on the inert solvent that is used, as long as this solvent does not participate in the reaction. Examples of solvents that can be used include alcohol type solvents such as methanol, ethanol, n-propanol, i-propanol, n-butanol, s-butanol, t-butanol, pentanol, hexanol, cyclopropanol, cyclobutanol, cyclopentanol, cyclohexanol, ethylene glycol, 1,3-propanediol, 1,4-butanediol and 1,5-pentanediol; halogen type solvents such as dichloromethane, chloroform and carbon tetrachloride; ether type solvents such as diethyl ether, tetrahydrofuran, dioxane and dimethoxyethane; aromatic solvents such as benzene, toluene, xylene, quinoline and chlorobenzene; and other solvents such as cyclohexane, dimethylsulfoxide, dimethylacetamide, dimethylimidazolidinone, dimethylformamide, N-methylpyrrolidone, acetonitrile and the like. Especially suitable are alcohol type solvents such as methanol, ethanol, n-propanol, i-propanol, n-butanol, s-butanol, t-butanol, pentanol, hexanol, cyclopropanol, cyclobutanol, cyclopentanol, cyclohexanol, ethylene glycol, 1,3-propanediol, 1,4-butanediol and 1,5-pentanediol; and ether type solvents such as diethyl ether, tetrahydrofuran, dioxane and dimethoxyethane; furthermore, ethanol, dioxane and the like are even more preferable.

There are no particular restrictions on the acid used. However, examples of acids that can be used include hydrochloric acid, sulfuric acid, methanesulfonic acid and the like. Here, hydrochloric acid, sulfuric acid and the like are especially suitable.

The reaction temperature varies according to the type of solvent used and the like, but is ordinarily 0° C. to 200° C., and is preferably 20° C. to 150° C. The reaction time varies according to the reaction temperature and the like, but is ordinarily 10 minutes to 48 hours, and is preferably 30 minutes to 24 hours.

The compounds of the present invention can also be manufactured by method B shown below:

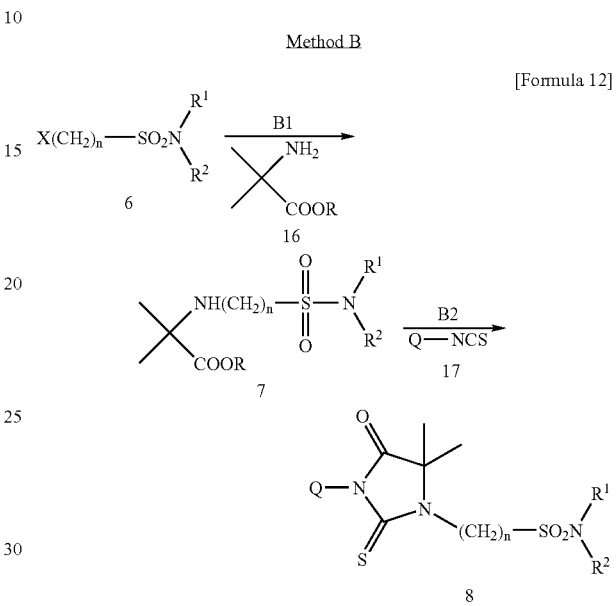

[Formula 12]

wherein X, Q, $R^1$, $R^2$, R and n are as defined hereinbefore.

Method B is a method for manufacturing compound 8, which is a compound represented by general formula (I) in which $R^1$ and $R^2$ may be the same or different, and are a hydrogen atom or a $C_1$-$C_6$ alkyl group.

Step B1 is a step for manufacturing compound 7; this is accomplished by reacting compound 6 and compound 16 in the presence of a base, with or without additive, in an inert solvent, and is performed in the same manner as step A2 of method A.

Step B2 is a step for manufacturing compound 8; this is accomplished by reacting compound 7 and compound 17 in the presence of a base or without a base in an inert solvent, and is performed in the same manner as step A3 of method A.

The compounds of the present invention can also be manufactured by method C shown below:

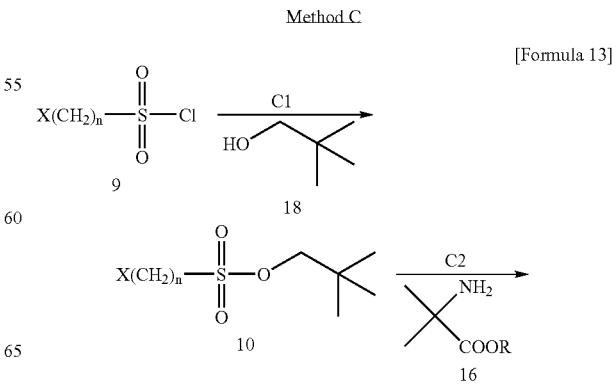

[Formula 13]

-continued

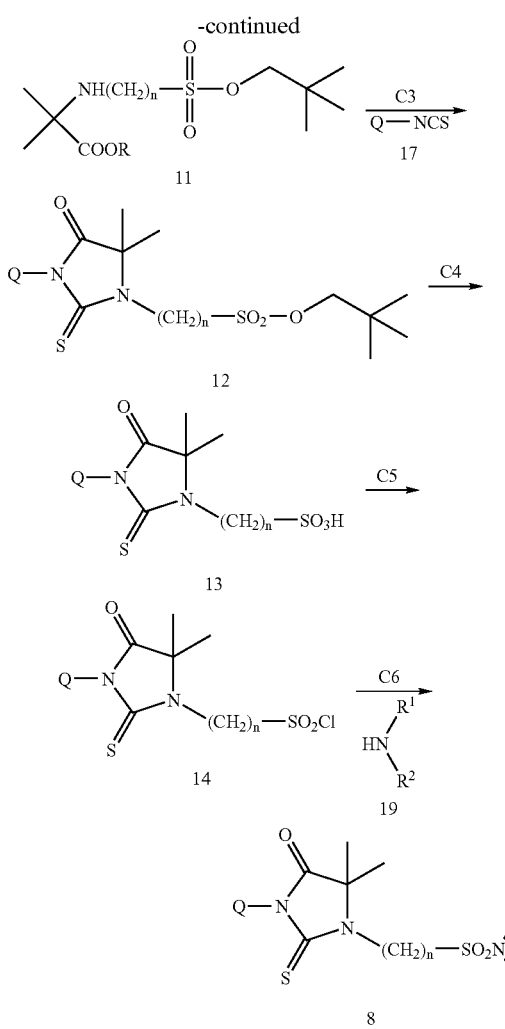

wherein X, Q, $R^1$, $R^2$, R and n are as defined hereinbefore.

Method C is another method for manufacturing compound 8, which is a compound represented by general formula (I) in which $R^1$ and $R^2$ may be the same or different, and are a hydrogen atom or a $C_1$-$C_6$ alkyl group.

Step C1 is a step for manufacturing compound 10; this is accomplished by reacting compound 9 and compound 18 in the presence of a base in an inert solvent. The alcohol used in this step may be a linear or branched alkyl alcohol with 1 to 6 carbon atoms, or a linear or branched aralkyl alcohol or aryl alcohol with 1 to 3 carbon atoms. For example, methanol, ethanol, n-propanol, isopropanol, t-butanol, neopentyl alcohol (compound 18), benzyl alcohol or the like may be used.

There are no particular restrictions on the inert solvent that is used, as long as this solvent does not participate in the reaction. Examples of solvents that can be used include halogen type solvents such as dichloromethane, chloroform and carbon tetrachloride; ether type solvents such as diethyl ether, tetrahydrofuran, dioxane and dimethoxyethane; aromatic solvents such as benzene, toluene, xylene, quinoline and chlorobenzene; and other solvents such as cyclohexane, dimethylsulfoxide, dimethylacetamide, dimethylimidazolidinone, dimethylformamide, N-methylpyrrolidone, acetonitrile and the like. Most suitable are halogen type solvents such as dichloromethane, chloroform and carbon tetrachloride, and ether type solvents such as diethyl ether, tetrahydrofuran, dioxane and dimethoxyethane; and dichloromethane and the like are especially preferable.

Examples of bases that can be used include amines such as triethylamine, diisopropylethylamine, 1,8-diazabicyclo[5.4.0]-7-undecene, pyridine, dimethylaminopyridine and pyrazine. Preferably, the base used is triethylamine, dimethylaminopyridine or the like.

The reaction temperature varies according to the type of solvent used and the like, but is ordinarily −30° C. to 100° C., and is preferably −10° C. to 30° C. The reaction time varies according to the reaction temperature and the like, but is ordinarily 10 minutes to 48 hours, and is preferably 30 minutes to 24 hours.

Step C2 is a step for manufacturing compound 11; this is accomplished by reacting compound 10 and compound 16 in the presence of a base, with or without additives, in an inert solvent. This step is performed in the same manner as step A2 of method A.

Step C3 is a step for manufacturing compound 12; this is accomplished by reacting compound 11 and compound 17 in the presence of a base or without a base in an inert solvent. This step is performed in the same manner as step A3 of method A.

Step C4 is a step for manufacturing compound 13; this is accomplished by reacting compound 12 with tetramethylammonium chloride or the like in an inert solvent.

There are no particular restrictions on the inert solvent that is used, as long as this solvent does not participate in the reaction. Examples of solvents that can be used include halogen type solvents such as dichloromethane, chloroform and carbon tetrachloride; ether type solvents such as diethyl ether, tetrahydrofuran, dioxane and dimethoxyethane; aromatic solvents such as benzene, toluene, xylene, quinoline and chlorobenzene; and other solvents such as cyclohexane, dimethylsulfoxide, dimethylacetamide, dimethylimidazolidinone, dimethylformamide, N-methylpyrrolidone, acetonitrile and the like. Most suitable are dimethylsulfoxide, dimethylacetamide, dimethylimidazolidinone, dimethylformamide, N-methylpyrrolidone, acetonitrile and the like, and dimethylformamide and the like are especially preferable.

The reaction temperature varies according to the type of solvent used and the like, but is ordinarily 30° C. to 250° C., and is preferably 80° C. to 230° C. The reaction time varies according to the reaction temperature and the like, but is ordinarily 10 minutes to 48 hours, and is preferably 30 minutes to 24 hours.

Step C5 is a step for manufacturing compound 14; this is accomplished by reacting a salt formed by compound 13 and a base such as triethylamine or the like with a reagent such as triphenylphosphine-thionyl chloride or the like in an inert solvent.

There are no particular restrictions on the inert solvent that is used, as long as this solvent does not participate in the reaction. Examples of solvents that can be used include halogen type solvents such as dichloromethane, chloroform and carbon tetrachloride; ether type solvents such as diethyl ether, tetrahydrofuran, dioxane and dimethoxyethane; aromatic solvents such as benzene, toluene, xylene, quinoline and chlorobenzene; and other solvents such as cyclohexane, dimethylsulfoxide, dimethylacetamide, dimethylimidazolidinone, dimethylformamide, N-methylpyrrolidone, acetonitrile and the like. Most suitable are halogen type solvents such as dichloromethane, chloroform and carbon tetrachloride, and ether type solvents such as diethyl ether, tetrahydrofuran, dioxane and dimethoxyethane, and dichloromethane and the like are especially preferable.

The reaction temperature varies according to the type of solvent used and the like, but is ordinarily −30° C. to 50° C., and is preferably 0° C. to 30° C. The reaction time varies according to the reaction temperature and the like, but is ordinarily 10 minutes to 48 hours, and is preferably 30 minutes to 24 hours.

Step C6 is a step for manufacturing compound 8; this is accomplished by reacting compound 14 and compound 19 in an inert solvent.

There are no particular restrictions on the inert solvent that is used, as long as this solvent does not participate in the reaction. Examples of solvents that can be used include halogen type solvents such as dichloromethane, chloroform and carbon tetrachloride; ether type solvents such as diethyl ether, tetrahydrofuran, dioxane and dimethoxyethane; aromatic solvents such as benzene, toluene, xylene, quinoline and chlorobenzene; and other solvents such as cyclohexane, dimethylsulfoxide, dimethylacetamide, dimethylimidazolidinone, dimethylformamide, N-methylpyrrolidone, acetonitrile and the like. Most suitable are halogen type solvents such as dichloromethane, chloroform and carbon tetrachloride, and ether type solvents such as diethyl ether, tetrahydrofuran, dioxane and dimethoxyethane, and dichloromethane and the like are especially preferable.

The reaction temperature varies according to the type of solvent used and the like, but is ordinarily −30° C. to 50° C., and is preferably 0° C. to 30° C. The reaction time varies according to the reaction temperature and the like, but is ordinarily 10 minutes to 48 hours, and is preferably 30 minutes to 24 hours.

The compounds of the present invention can also be manufactured by method D shown below:

Method D

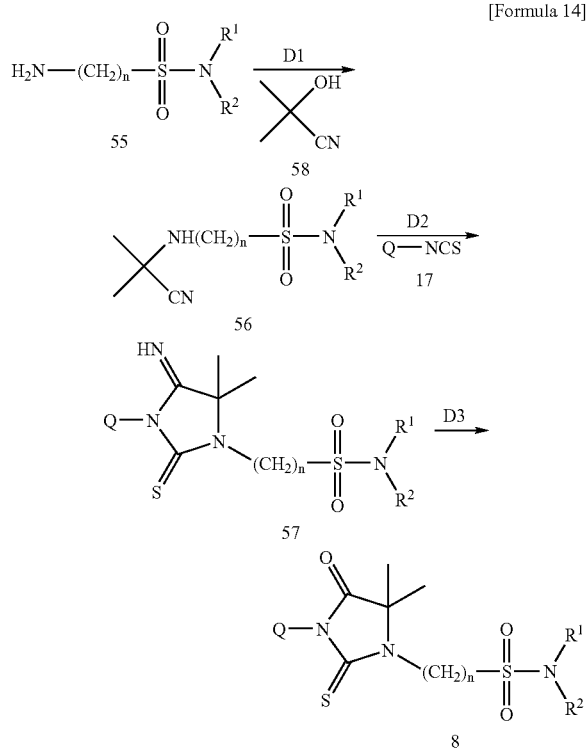

[Formula 14]

wherein Q, R$^1$, R$^2$ and n are as defined hereinbefore.

Method D is another method for manufacturing compound 8, which is a compound represented by general formula (I) in which R$^1$ and R$^2$ may be the same or different, and are a hydrogen atoms or a C$_1$-C$_6$ alkyl group.

Step D1 is a step for manufacturing compound 56, and is achieved by reacting compound 55 with compound 58 in the inert solvent.

There are no particular restrictions on the inert solvent that is used, as long as this solvent does not participate in the reaction. Examples of solvents that can be used include ether type solvents such as diethyl ether, tetrahydrofuran, dioxane and dimethoxyethane; alcohol type solvents such as methanol, ethanol, n-propanol, i-propanol, n-butanol, s-butanol, t-butanol, pentanol, hexanol, cyclopropanol, cyclobutanol, cyclopentanol, cyclohexanol, ethylene glycol, 1,3-propanediol, 1,4-butanediol and 1,5-pentanediol; and other solvents such as dimethylsulfoxide, dimethylacetamide and the like. Most suitable are methanol, ethanol, diethyl ether and the like, and methanol is especially preferable.

The reaction temperature varies depending on the type of solvent used and the like, but is ordinarily 0° C. to 200° C., and is preferably 10° C. to 100° C. The reaction time varies according to the reaction temperature and the like, but is ordinarily 10 minutes to 48 hours, and is preferably 30 minutes to 24 hours.

Step D2 is a step for manufacturing compound 57; this is accomplished by reacting compound 56 and compound 17 in the presence of a base or without a base in an inert solvent.

There are no particular restrictions on the inert solvent that is used, as long as this solvent does not participate in the reaction. Examples of solvents that can be used include halogen type solvents such as dichloromethane, chloroform and carbon tetrachloride; ether type solvents such as diethyl ether, tetrahydrofuran, dioxane and dimethoxyethane; aromatic solvents such as benzene, toluene, xylene, quinoline and chlorobenzene; and other solvents such as cyclohexane, dimethylsulfoxide, dimethylacetamide, dimethylimidazolidinone, dimethylformamide, N-methylpyrrolidone, acetonitrile and the like. Most suitable are halogen type solvents such as dichloromethane, chloroform and carbon tetrachloride, and ether type solvents such as diethyl ether, tetrahydrofuran, dioxane and dimethoxyethane, and dichloromethane, tetrahydrofuran and the like are especially preferable.

Examples of bases that can be used include amines such as triethylamine, diisopropylethylamine, 1,8-diazabicyclo[5.4.0]-7-undecene, pyridine, dimethylaminopyridine and pyrazine. Preferably, the base used is triethylamine, dimethylaminopyridine or the like. Such a base may be used or omitted. However, the use of a base is preferable.

The reaction temperature varies depending on the type of solvent used and the like, but is ordinarily −30° C. to 100° C., and is preferably 0° C. to 50° C. The reaction time varies according to the reaction temperature and the like, but is ordinarily 10 minutes to 48 hours, and is preferably 30 minutes to 24 hours.

Step D3 is a step for manufacturing compound (8); this is accomplished by hydrolyzing compound (57) with an acid in an inert solvent.

There are no particular restrictions on the inert solvent that is used, as long as this solvent does not participate in the reaction. Examples of solvents that can be used include alcohol type solvents such as methanol, ethanol, n-propanol, i-propanol, n-butanol, s-butanol, t-butanol, pentanol, hexanol, cyclopropanol, cyclobutanol, cyclopentanol, cyclohexanol, ethylene glycol, 1,3-propanediol, 1,4-butanediol and 1,5-pentanediol; halogen type solvents such as dichloromethane, chloroform and carbon tetrachloride; ether type solvents such as diethyl ether, tetrahydrofuran, dioxane and dimethoxyethane; aromatic solvents such as benzene, toluene, xylene, quinoline and chlorobenzene; and other solvents such as cyclohexane, dimethylsulfoxide, dimethylacetamide, dimethylimidazolidinone, dimethylformamide, N-methylpyrrolidone, acetonitrile and the like. Most suitable are alcohol type solvents such as methanol, ethanol, n-propanol, i-propanol, n-butanol, s-butanol, t-butanol, pentanol, hexanol, cyclopropanol, cyclobutanol, cyclopentanol, cyclohexanol, ethylene glycol, 1,3-propanediol, 1,4-butanediol and 1,5-pentanediol, and ether type solvents such as diethyl ether, tetrahydrofuran, dioxane and dimethoxyethane; furthermore, dioxane and the like are especially preferable.

There are no particular restrictions on the acid used. However, examples of acids that can be used include hydrochloric acid, sulfuric acid and the like. Here, hydrochloric acid and the like are especially preferable.

The reaction temperature varies according to the type of solvent used and the like, but is ordinarily 0° C. to 200° C., and is preferably 20° C. to 150° C. The reaction time varies according to the reaction temperature and the like, but is ordinarily 10 minutes to 48 hours, and is preferably 30 minutes to 24 hours.

Compound 17, which is an intermediate used to synthesize the compounds of the present invention, can be manufactured by method E shown below:

Method E

[Formula 15]

wherein Q is as defined hereinbefore.

For example, compound 17 can be manufactured according to the method described in The Journal of Steroid Biochemistry and Molecular Biology, Vol. 48, No. 1, pp. 111-119, 1994.

Step E1 is accomplished by reacting compound 68 with thiophosgene in an inert solvent. There are no particular restrictions on the inert solvent that is used, as long as this solvent does not participate in the reaction. Examples of solvents that can be used include halogen type solvents such as dichloromethane, chloroform and carbon tetrachloride; ether type solvents such as diethyl ether, tetrahydrofuran, dioxane and dimethoxyethane; aromatic solvents such as benzene, toluene, xylene, quinoline and chlorobenzene; and other solvents such as cyclohexane, dimethylsulfoxide, dimethylacetamide, dimethylimidazolidinone, dimethylformamide, N-methylpyrrolidone, acetonitrile and the like. Most suitable are dichloromethane, diethyl ether, tetrahydrofuran, dioxane and the like, and tetrahydrofuran and the like are especially preferable.

The reaction temperature varies depending on the type of solvent used and the like, but is ordinarily −30° C. to 100° C., and is preferably 0° C. to 50° C. The reaction time varies depending on the reaction temperature and the like, but is ordinarily 10 minutes to 48 hours, and is preferably 30 minutes to 24 hours.

On the other hand, step E1 can be also carried out by using a di($C_1$-$C_6$ alkyl)thiocarbamoyl chloride such as dimethylcarbamoyl chloride. In such a case, compound 17 can be obtained by reacting compound 68 with a di($C_1$-$C_6$ alkyl) carbamoyl chloride in an inert solvent in the presence or absence of an acid.

The compounds of the present invention can also be manufactured by method F shown below:

Method F

[Formula 16]

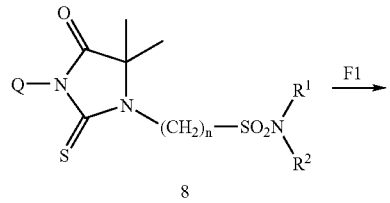

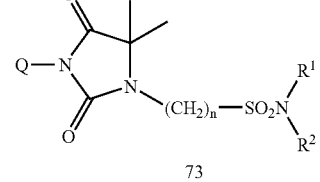

wherein Q, $R^1$, $R^2$ and n are as defined hereinbefore.

Method F is a method for manufacturing compound 73 in which $X^1$ and $X^2$ are both O (among the compounds represented by general formula I).

Step F1 is a step for manufacturing compound 73; this is accomplished by reacting compound 8 with an oxidizing agent in an inert solvent (which may be a single solvent or a mixture of a plurality of solvents).

There are no particular restrictions on the inert solvent that is used, as long as this solvent does not participate in the reaction. Examples of solvents that can be used include halogen type solvents such as dichloromethane, chloroform and carbon tetrachloride; ether type solvents such as diethyl ether, tetrahydrofuran, dioxane and dimethoxyethane; aromatic solvents such as benzene, toluene, xylene, quinoline and chlorobenzene, and other solvents such as cyclohexane, dimethylsulfoxide, dimethylacetamide, dimethylimidazolidinone, dimethylformamide, N-methylpyrrolidone, acetonitrile, water and the like. Most suitable is a mixed solvent of carbon tetrachloride, acetonitrile and water or the like.

There are no particular restrictions on the oxidizing agent used; for example, the oxidizing agents shown below can be used.

Halogens: chlorine, bromine, iodine, hypochloric acid, sodium hypochlorite, potassium hypobromite, potassium hypoiodite, sodium chlorate, potassium chlorate, sodium bromate, potassium bromate, sodium iodate, potassium iodate, perchloryl fluoride, ortho-periodic acid, sodium meta-periodate, potassium meta-periodate, N-bromoacetamide, N-bromosuccinimide, N-bromophthalimide, isocyanuric chloride, isocyanuric bromide, N-bromocaprolactam, 1-chlorobenzotriazole, 1,3-dibromo-5,5-dimethylhydantoin, sodium N-chloro-p-toluene sulfonamide (chloramine T), sodium N-chlorobenzene sulfonamide (chloramine B), t-butyl hypochlorite, t-butyl hypobromite, t-butyl hypoiodite, iodosylbenzene acetate, iodosylbenzene and the like;

Manganese compounds: potassium permanganate, manganese dioxide, manganese (III) acetate, manganese (III) tris (acetonylacetonite) (MTA), manganese (III) sulfate, manganese (III) pyrophosphate and the like;

Chromium compounds: chromium (IV) oxide, Jones' reagent, Sarett's reagent, Collins' reagent, chromic acid t-butyl ester, potassium bichromate, Beckmann's mixed liquid, sodium bichromate, Kiliani's reagent, chromyl chloride, chromyl acetate, pyridinium chorochromate (PCC), pyridinium dichromate (PDC) and the like;

Lead compounds: lead tetraacetate, lead tetrabenzoate, red lead, lead oxide (IV), lead dioxide, and the like;

Mercury compounds: mercury (II) acetate, mercury (II) trifluoroacetate, anhydrous mercury (II) nitrate, mercury (II) oxide and the like;

Organic per-acids: t-butyl perbenzoate, t-butyl peracetate, organic peroxides such as t-butylhydroperoxide, t-amyl hydroperoxide, dibenzoyl peroxide, di-p-nitrobenzoyl peroxide and di-p-chlorobenzoyl peroxide, perbenzoic acid, meta-chloroperbenzoic acid, p-nitroperbenzoic acid, monoperoxyphthalic acid, performic acid, peracetic acid, trifluoroperacetic acid, peroxylauric acid and the like;

Nitrogen oxides: nitric acid, nitrous acid, nitrosyl chloride, nitrous oxide, dinitrogen trioxide, dinitrogen tetraoxide, potassium nitrosodisulfonate (Fremy's salt) and the like;

Quinones: 2,3-dichloro-5,6-dicyano-1,4-benzoquinone (DDQ), tetrachloro-1,2-benzoquinone (o-choranil), tetrachloro-1,4-benzoquinone (chloranil) and the like;

Alkyl nitrites: ethyl nitrite, n-butyl nitrite, isoamyl nitrite and the like;

Silver compounds: silver (I) oxide, silver nitrate, silver carbonate (Fetizon's reagent) and the like;

Copper compounds: copper (I) chloride, copper (II) chloride, copper acetate, copper (II) oxide, copper sulfate-pyridine and the like;

Iron compounds: iron (III) chloride, potassium ferricyanide, iron (III) sulfate and the like;

Other: ruthenium (III) chloride-sodium meta-periodate, hydrogen peroxide, dimethylsulfoxide, oxygen and the like.

Examples of preferable oxidizing agents include halogens such as chlorine, bromine, iodine, hypochloric acid, sodium hypochlorite, potassium hypobromite, potassium hypoiodite, sodium chlorate, potassium chlorate, sodium bromate, potassium bromate, sodium iodate, potassium iodate, perchloryl fluoride, ortho-periodic acid, sodium meta-periodate, potassium meta-periodate, N-bromoacetamide, N-bromosuccinimide, N-bromophthalimide, isocyanuric chloride, isocyanuric bromide, N-bromocaprolactam, 1-chlorobenzotriazole, 1,3-dibromo-5,5-dimethylhydantoin, sodium N-chloro-p-toluene sulfonamide (chloramine T), sodium N-chlorobenzene sulfonamide (chloramine B), t-butyl hypochlorite, t-butyl hypobromite, t-butyl hypoiodite, iodosylbenzene acetate, iodosylbenzene and the like; manganese compounds such as potassium permanganate, manganese dioxide, manganese (III) acetate, manganese (III) tris(acetonylacetonite) (MTA), manganese (III) sulfate, manganese (III) pyrophosphate and the like; and other compounds such as ruthenium (III) chloride-sodium meta-periodate, hydrogen peroxide, dimethylsulfoxide, oxygen and the like. Especially preferable oxidizing agents are potassium permanganate, ruthenium (III) chloride-sodium meta-periodate, hydrogen peroxide, dimethylsulfoxide, oxygen and the like.

The reaction temperature varies according to the type of solvent used and the like, but is ordinarily −30° C. to 100° C., and is preferably 0° C. to 50° C. The reaction time varies according to the reaction temperature and the like, but is ordinarily 10 minutes to 48 hours, and is preferably 30 minutes to 24 hours.

The compounds of the present invention can also be manufactured by method G shown below:

Method G

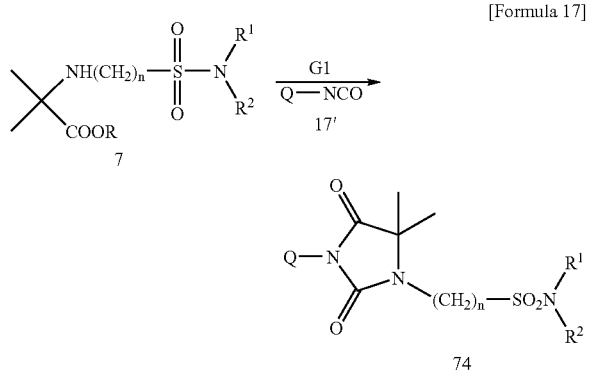

[Formula 17]

wherein Q, $R^1$, $R^2$, R and n are as defined hereinbefore.

Method G is a method for manufacturing compound 74, which is a compound represented by general formula (I), in which both $X^1$ and $X^2$ are O.

Step G1 is a step for manufacturing compound 74, which is accomplished by reacting compound 7 and compound 17' in the presence or absence of a base in an inert solvent.

There are no particular restrictions on the inert solvent that is used, as long as this solvent does not participate in the reaction. Examples of solvents that can be used include halogen type solvents such as dichloromethane, chloroform and carbon tetrachloride; ether type solvents such as diethyl ether, tetrahydrofuran, dioxane and dimethoxyethane; aromatic solvents such as benzene, toluene, xylene, quinoline and chlorobenzene; and other solvents such as cyclohexane, dimethylsulfoxide, dimethylacetamide, dimethylimidazolidinone, dimethylformamide, N-methylpyrrolidone, acetonitrile and the like. Most suitable are halogen type solvents such as dichloromethane, chloroform and carbon tetrachloride, and ether type solvents such as diethyl ether, tetrahydrofuran, dioxane and dimethoxyethane. Furthermore, dichloromethane, tetrahydrofuran and the like are especially suitable.

Examples of bases that can be used include amines such as triethylamine, diisopropylethylamine, 1,8-diazabicyclo[5.4.0]-7-undecene, pyridine, dimethylaminopyridine and pyrazine. Preferably, the base used is triethylamine, dimethylaminopyridine or the like. Such a base may be used or omitted. However, the use of a base is preferable.

The reaction temperature varies according to the type of solvent used and the like, but is ordinarily −30° C. to 100° C., and is preferably 0° C. to 50° C. The reaction time varies according to the reaction temperature and the like, but is ordinarily 10 minutes to 48 hours, and is preferably 30 minutes to 24 hours.

Furthermore, the isocyanate of compound 17' can be manufactured by reacting the arylamine of the abovementioned compound 68 with triphosgene, or from the corresponding carboxylic acid via a Hoffman rearrangement or Curtius rearrangement.

Compound 107, which is an intermediate used to synthesize the compounds of the present invention, can be manufactured by method H shown below:

Method H

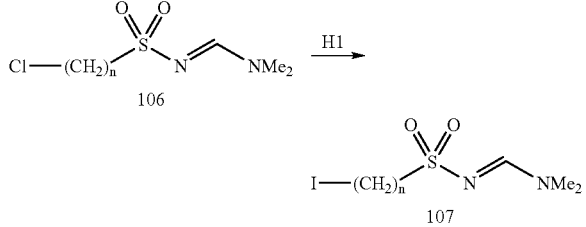

[Formula 18]

wherein n is as defined hereinbefore.

Step H1 is a step for manufacturing compound 107, which is accomplished by reacting compound 106 with an iodizing agent.

There are no particular restrictions on the inert solvent that is used, as long as this solvent does not participate in the reaction. Examples of solvents that can be used include ketones such as acetone and methyl ethyl ketone; ether type solvents such as ether, tetrahydrofuran, dioxane and dimethoxyethane; aromatic solvents such as benzene, toluene, xylene, quinoline and chlorobenzene; halogen type solvents such as dichloromethane, chloroform and carbon tetrachloride; and other solvents such as acetonitrile, cyclohexane, dimethylsulfoxide, dimethylacetamide, dimethylimidazolidinone, dimethylformamide, N-methylpyrrolidone, ethyl acetate and the like. Most suitable are acetone and the like.

There are no particular restrictions on the iodizing agent that is used; examples of such agents include sodium iodide and the like.

The reaction temperature varies according to the type of solvent used and the like, but is ordinarily 0° C. to 100° C., and is preferably 5° C. to 50° C. The reaction time varies according to the reaction temperature and the like, but is ordinarily 10 minutes to 48 hours, and is preferably 30 minutes to 24 hours.

The compounds of the present invention can also be manufactured by method I shown below:

Method I

[Formula 19]

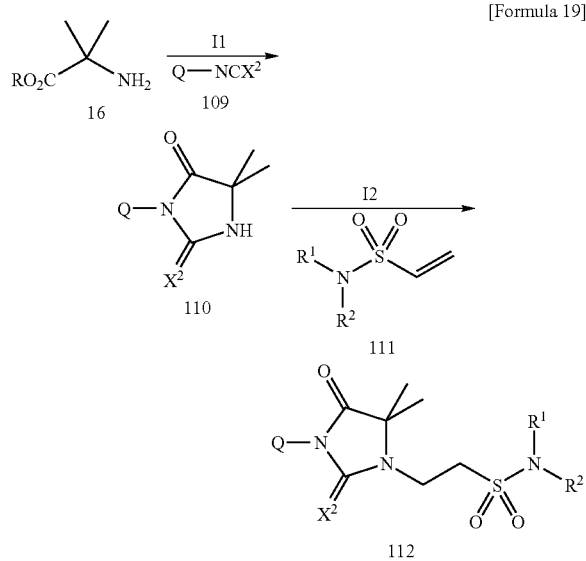

wherein Q, R, $R^1$, $R^2$ and $X^2$ are as defined hereinbefore.

Method I is a method for manufacturing compound 112 in which n is 2 (among the compounds represented by formula (I)).

Step I1 is a step for manufacturing compound 110, which is accomplished by reacting compound 16 and compound 109 in the presence or absence of a base in an inert solvent. This step is the same as step A3 of method A.

Step I2 is a step for manufacturing compound 112, which is accomplished by reacting compound 110 and compound III in the presence of a base in an inert solvent.

There are no particular restrictions on the inert solvent that is used, as long as this solvent does not participate in the reaction. Examples of solvents that can be used include ether type solvents such as ether, tetrahydrofuran, dioxane and dimethoxyethane; aromatic solvents such as benzene, toluene, xylene, quinoline and chlorobenzene; halogen type solvents such as dichloromethane and carbon tetrachloride; and other solvents such as acetonitrile, cyclohexane, dimethylsulfoxide, dimethylacetamide, 1,3-dimethyl-2-imidazolinone, dimethylformamide, N-methylpyrrolidone, ethyl acetate and the like. Most suitable are 1,3-dimethyl-2-imidazolinone, dimethylformamide and the like.

There are no particular restrictions on the base that is used; examples of bases that can be used include carbonates such as potassium carbonate, sodium carbonate and cesium carbonate; metal hydrides such as sodium hydride, potassium hydride and calcium hydride, and the like, and more preferably potassium carbonate or sodium hydride and the like.

The reaction temperature varies according to the type of solvent used and the like, but is ordinarily 0° C. to 200° C., and is preferably 5° C. to 150° C. The reaction time varies according to the reaction temperature and the like, but is ordinarily 10 minutes to 48 hours, and is preferably 30 minutes to 24 hours.

Compound 114, which is an intermediate that is used to synthesize the compounds of the present invention, can be manufactured by method J shown below:

Method J

[Formula 20]

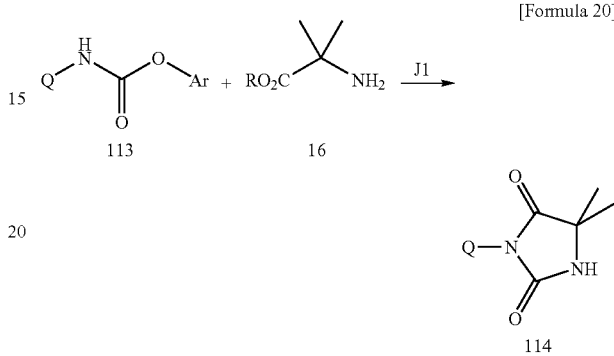

wherein Ar is an aromatic group such as a phenyl group or p-nitrophenyl group, and Q and R are as defined hereinbefore.

Step J1 is a step for manufacturing compound 114, and is accomplished by reacting compound 113 and compound 16 in the presence of a base in an inert solvent.

There are no particular restrictions on the inert solvent that is used, as long as this solvent does not participate in the reaction. Examples of solvents that can be used include ether type solvents such as ether, tetrahydrofuran, dioxane and dimethoxyethane; aromatic solvents such as benzene, toluene, xylene, quinoline and chlorobenzene; halogen type solvents such as dichloromethane and carbon tetrachloride; and other solvents such as acetonitrile, cyclohexane, dimethyl sulfoxide, dimethylacetamide, 1,3-dimethyl-2-imidazolidinone, dimethylformamide, N-methylpyrrolidone, ethyl acetate and the like. Most suitable are dichloromethane, dioxane, toluene and the like.

There are no particular restrictions on the base that is used; examples of bases that can be used include amines such as triethylamine, diisopropylethylamine, 1,8-diazabicyclo[5.4.0]-7-undecene, pyridine and dimethylaminopyridine. Preferably, the base used is diisopropylethylamine, 1,8-diazabicyclo[5.4.0]-7-undecene or the like.

The reaction temperature varies depending on the type of solvent used and the like, but is ordinarily −30° C. to 200° C., and is preferably −5° C. to 50° C. The reaction time varies depending on the reaction temperature and the like, but is ordinarily 10 minutes to 48 hours, and is preferably 30 minutes to 24 hours.

The compounds of the present invention can also be manufactured by method K shown below:

Method K

[Formula 21]

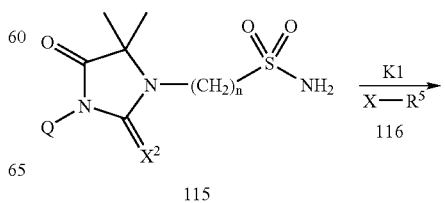

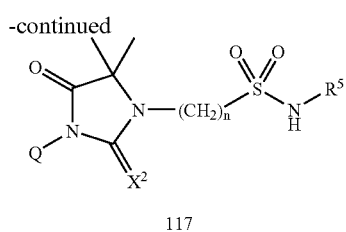

wherein $R^5$ is a $C_1$-$C_6$ acyl group, and n, Q and $X^2$ are as defined hereinbefore.

Step K1 is a step for manufacturing compound 117, and is accomplished by reacting compound 115 and compound 116 in the presence of a base in an inert solvent.

There are no particular restrictions on the inert solvent that is used, as long as this solvent does not participate in the reaction. Examples of solvents that can be used include ether type solvents such as ether, tetrahydrofuran, dioxane and dimethoxyethane; aromatic solvents such as benzene, toluene, xylene, quinoline and chlorobenzene; halogen type solvents such as dichloromethane, chloroform and carbon tetrachloride; and other solvents such as acetonitrile, cyclohexane, dimethyl sulfoxide, dimethylacetamide, 1,3-dimethyl-2-imidazolidinone, dimethylformamide, N-methylpyrrolidone, ethyl acetate and the like. Most suitable are 1,3-dimethyl-2-imidazolidinone, dimethylformamide and the like.

There are no particular restrictions on the base that is used; examples of bases that can be used include carbonates such as potassium carbonate and sodium carbonate, metal hydrides such as sodium hydride, potassium hydride and calcium hydride, and the like. Preferably, sodium hydride and the like is used.

The reaction temperature varies depending on the type of solvent used and the like, but is ordinarily 0° C. to 200° C., and is preferably 5° C. to 150° C. The reaction time varies according to the reaction temperature and the like, but is ordinarily 10 minutes to 48 hours, and is preferably 30 minutes to 24 hours.

In cases where groups requiring protection and deprotection are present in the respective processes of the abovementioned methods A through K, these respective groups can be subjected to protection and deprotection by method that are well known to persons skilled in the art. For example, in such protection and deprotection, reference may be made to "Protective Groups in Organic Synthesis $2^{nd}$ Edition", Theodora W. Green, John Wiley & Sons, Inc., 1991 or the like.

Methods used to manufacture the compounds of the present invention are not limited to the abovementioned methods. For example, the compounds of the present invention can also be synthesized by appropriately combining processes included in methods A through K.

Effect of the Invention

The present invention makes it possible to provide imidazolidine derivatives that can be an antiandrogen that shows no occurrence of androgen resistance as a result of long-term administration, and/or side effects such as liver toxicity or the like. Furthermore, the compounds of the present invention are also superior to existing compounds in terms of characteristics required in drugs, such as water solubility and the like, and therefore show promise as practical drugs.

EXAMPLES

Preferred examples of the present invention will be described in detail below. However, the present invention is not limited to these examples.

NMR was measured using a nuclear magnetic resonance apparatus ARX 300 (manufactured by Bruker), Mercury 300 (manufactured by Varian), ECP-400 (manufactured by JEOL) or EX270 (manufactured by JEOL). Furthermore, mass analysis was performed using a mass analysis apparatus Q-micro, Triple Quadrupole Mass Spectrometer (manufactured by MICROMASS), LCQ classic (manufactured by Thermo Electron), ZQ2000 (manufactured by Waters) or QP5050A (manufactured by Shimazu Seisakusho). Furthermore, Rf values in thin-layer chromatography were measured using a silica gel plate Silica gel 60 $F_{234}$ (manufactured by Merck).

The above compound 1, compound 6, compound 55 and compound III, which are starting materials used to synthesize the compounds of the present invention, are either universally known, or can easily be manufactured by publicly known methods or methods similar to such publicly known methods (e.g., [see] The Journal of Organic Chemistry, Vol. 52, No. 11, pp. 2162-2166, 1987; The Journal of Organic Chemistry, Vol. 58, No. 5, pp. 1128-1135, 1993; Bioorganic and Medicinal Chemistry Letters, Vol. 8, No. 13, pp. 1607-1612, 1998; Journal of Medicinal Chemistry, Vol. 31, No. 7, pp. 1421-1426 and the like).

The abovementioned compound 9, compound 15, compound 16, compound 18, compound 19 and compound 113, which are starting materials, are easily obtainable as commercially marketed products, or else are publicly known or can easily be manufactured by universally known methods or methods similar to these publicly known methods. Furthermore, compound 16 used in the present invention may be a salt such as a hydrochloride or the like. Hydrochloride salts are suitable for use.

Among the compounds indicated as compound 68, which is a starting material, compounds produced by the methyl substitution of 4-cyano-3-trifluoromethylaniline (compounds which are such that in compound 68-a, A is a cyano group, B is a trifluoromethyl group, m is 1, and E is a methyl group) were manufactured by the method shown below.

[Formula 22]

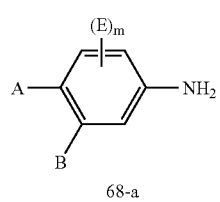

Reference Example 1

(First Step)

[Formula 23]

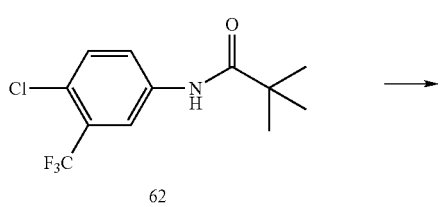

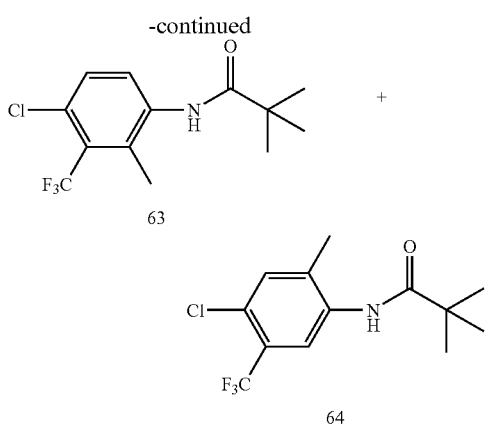

Compound 62 (11.15 g) was dissolved in tetrahydrofuran (123 mL), and an n-hexane solution of n-butyllithium (1.6 M, 60 mL) was added dropwise over a period of 20 minutes at −30° C. After stirring for 45 minutes at −30° C., methyl iodide (5.1 mL) was added dropwise. The reaction mixture was then stirred for 30 minutes at −30° C. Water was added, and an extraction was performed with ethyl acetate. The organic layer was dried over sodium sulfate, filtered, and concentrated under reduced pressure. The resulting residue was purified by silica gel column chromatography (developing solvent: dichloromethane) to give 8.63 g of compound 63 (known compound) (yield 74%) and 2.12 g of compound 64 (yield 18%).

Compound 64:
$^1$H-NMR (400 MHz, CDCl$_3$) δ: 1.35 (9H, s), 2.28 (3H, s), 7.32 (1H, s), 8.31 (1H, s).
MS (ESI): 294.1 ([M+H]$^+$).

(Second Step)

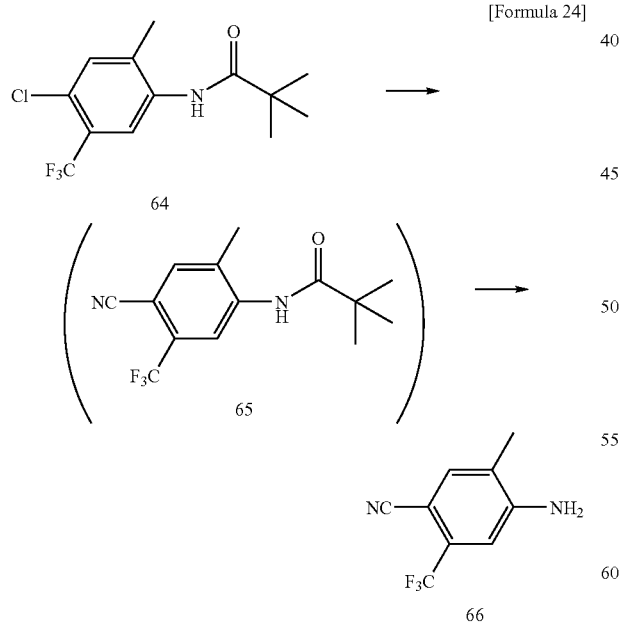

[Formula 24]

Compound 64 was dissolved in N-methylpyrrolidone (3.5 mL) and then, copper cyamide (177 mg) was added, and the reaction mixture was stirred for 4 days at 170° C. under a nitrogen atmosphere. Furthermore, copper cyamide (177 mg) and N-methylpyrrolidone (3.5 mL) were added, and the system was stirred for 7 days at 170° C. under a nitrogen atmosphere. After cooling, water was added, the deposited precipitate was collected, and this precipitated was vacuum-dried, to give a crude product of compound 65 (512 mg). This crude product was dissolved in ethanol (2.7 mL); concentrated hydrochloric acid (2.7 mL) was added, and the mixture was heated to reflux for 18 hours. Following cooling, the pH of the reaction solution was adjusted to a value of 9 to 11 by adding a 2 N aqueous solution of sodium hydroxide, and an extraction was then performed with dichloromethane. The organic layer was dried over sodium sulfate, filtered, and concentrated under reduced pressure. The resulting residue was purified by silica gel chromatography (developing solvent: dichloromethane) to give 46.1 mg of the desired compound (compound 66) (yield 20%).

$^1$H-NMR (400 MHz, CDCl$_3$) δ: 2.20 (3H, s), 4.30 (2H, brs), 6.94 (1H, s), 7.45 (1H, s).
MS (EI): 200 ([M]$^+$).

Reference Example 2

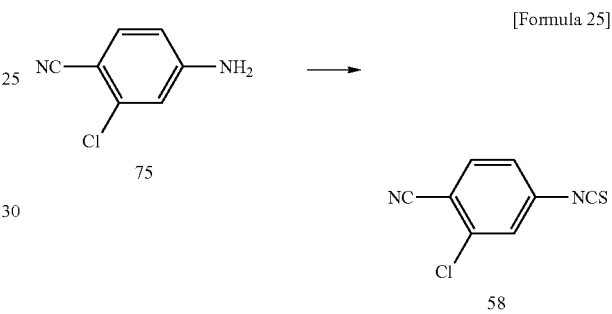

[Formula 25]

Under a nitrogen atmosphere, compound 75 (50 g) was dissolved in tetrahydrofuran (1500 mL), and this solution was cooled to 0° C. Thiophosgene (27.5 mL) was added, and the mixture was stirred for 1 hour at 5° C. Furthermore, water was added, and an extraction was performed twice with diethyl ether. The extract was then washed with brine, dried over anhydrous magnesium sulfate, filtered and concentrated under reduced pressure. The resulting residue was dissolved in a mixed solvent of ethyl acetate (50 mL) and hexane (600 mL), and this solution was allowed to stand for 1 hour at 5° C. Afterward, impurities were removed by decantation. The residue obtained by concentration under reduced pressure was recrystallized using acetone-hexane to give 44.5 g of the desired compound (compound 58) (yield 70%).

$^1$H-NMR (300 MHz, CDCl$_3$) δ: 7.19 (1H, dd, J=2.1, 8.7 Hz), 7.35 (1H, d, J=2.1 Hz), 7.65 (1H, d, J=8.7 Hz).

Reference Example 3

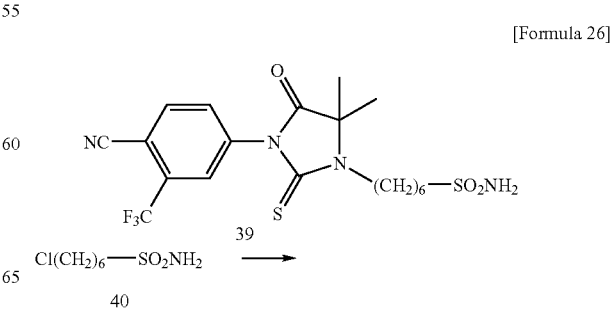

[Formula 26]

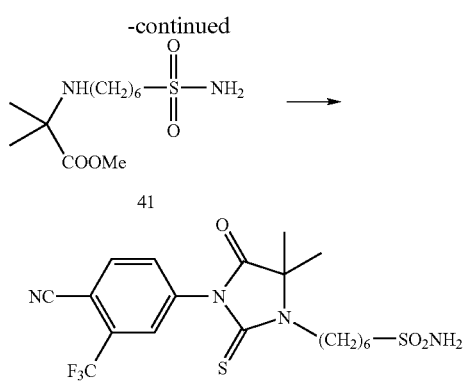

2-Aminoisobutyric acid methyl ester hydrochloride (215 mg) and potassium carbonate (406 mg) were dissolved in a mixed solvent of acetonitrile (2 mL) and dimethylformamide (0.4 mL), and this solution was stirred for 1.5 hours at room temperature. Compound 40 (93 mg) and tetra-n-butylammonium iodide (172 mg) were added, and the reaction mixture was heated to reflx for 19 hours. Following cooling, water was added, and an extraction was performed with ethyl acetate. The organic layer washed with brine, dried over magnesium sulfate, and filtered, and the solvent was distilled away under reduced pressure to give a crude product of compound 41 (94 mg). 4-Cyano-3-trifluoromethylphenyl isothiocyanate (54 mg) was dissolved in tetrahydrofuran (1 mL), the abovementioned crude product of compound 41 (94 mg) and triethylamine (0.006 mL) were added to this solution, and the resulting mixture was stirred for 7.5 hours at room temperature. The reaction solution was purified by silica gel column chromatography (developing solvent: ethyl acetate n-hexane=1:1 to 2:1) and reverse phase column chromatography (packing material: LiChroprep RP=18, developing solvent: methanol:water=2:3 to 1:1) to give 12 mg of the desired compound (compound 39) (yield: 5.4%).

$^1$H-NMR (300 MHz, CDCl$_3$) δ: 1.43-1.56 (4H, m), 1.61 (6H, s), 1.84-1.93 (4H, m), 3.11-3.16 (2H, m), 3.66-3.71 (2H, m), 4.68 (2H, s), 7.77 (1H, dd, J=1.9, 8.5 Hz), 7.90 (1H, d, J=1.9 Hz), 7.95 (1H, d, J=8.5 Hz).

Rf value (silica gel plate, developing solvent: ethyl acetate: n-hexane=1:1):0.07.

MS (ESI): 477.5 ([M+H]$^+$).

Reference Example 4

[Formula 27]

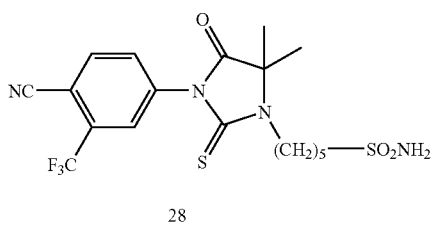

(First Step)

[Formula 28]

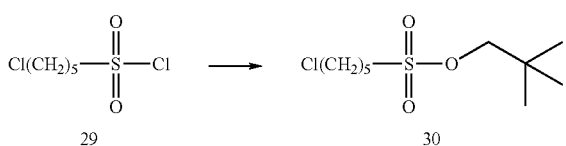

Compound 29 (2.05 g) and neopentyl alcohol (0.96 g) were dissolved in dichloromethane (20 mL), and this solution was cooled to 0° C. Triethylamine (4.6 mL) was added dropwise, and the resulting mixture was stirred for 2.5 hours at 0 to 5° C. The reaction solution washed with a saturated aqueous solution of sodium hydrogencarbonate, and the organic layer was dried over magnesium sulfate, filtered, and concentrated under reduced pressure. The resulting residue was purified by silica gel column chromatography (developing solvent: ethyl acetate:n-hexane=1:10) to give 743 mg of the desired compound (compound 30) (yield: 29%).

$^1$H-NMR (300 MHz, CDCl$_3$) δ: 0.99 (9H, s), 1.58-1.67 (2H, m), 1.78-1.96 (4H, m), 3.06-3.16 (2H, m), 3.55 (2H, t, J=6.5 Hz), 3.87 (2H, s).

Rf value (silica gel plate, developing solvent: ethyl acetate: n-hexane=1:9):0.53

(Second Step)

[Formula 29]

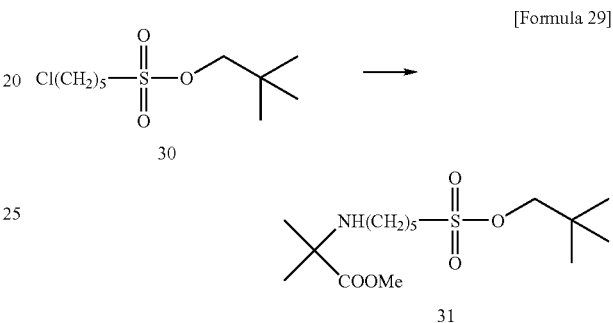

357 mg of the desired compound (compound 31) (yield: 37%) was obtained from compound 30 (743 mg) by the same method as in the second step of Example 1.

$^1$H-NMR (300 MHz, CDCl$_3$) δ: 0.99 (9H, s), 1.30 (6H, s), 1.48-1.60 (4H, m), 1.85-1.91 (2H, m), 2.43-2.48 (2H, m), 3.07-3.12 (2H, m), 3.70 (3H, s), 3.86 (2H, s).

Rf value (silica gel plate, developing solvent: ethyl acetate: n-hexane=1:1):0.35

(Third Step)

[Formula 30]

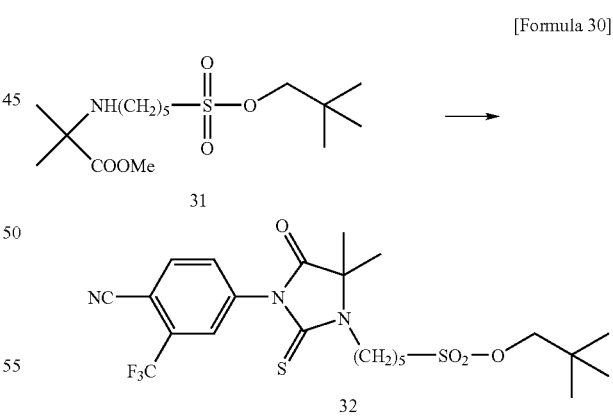

465 mg of the desired compound (compound 32) (yield: 82%) was obtained from compound 31 (357 mg) by the same method as in the third step of Example 1.

$^1$H-NMR (300 MHz, CDCl$_3$) δ: 0.99 (9H, s), 1.59 (6H, s), 1.50-1.62 (2H, m), 1.87-2.00 (4H, m), 3.15 (2H, t, J=7.6 Hz), 3.67-3.73 (2H, m), 3.88 (2H, s), 7.77 (1H, dd, J=1.6, 8.5 Hz), 7.89 (1H, d, J=1.6 Hz), 7.96 (1H, d, J=8.5 Hz).

Rf value (silica gel plate, developing solvent: ethyl acetate: n-hexane=1:1):0.40.

(Fourth Step)

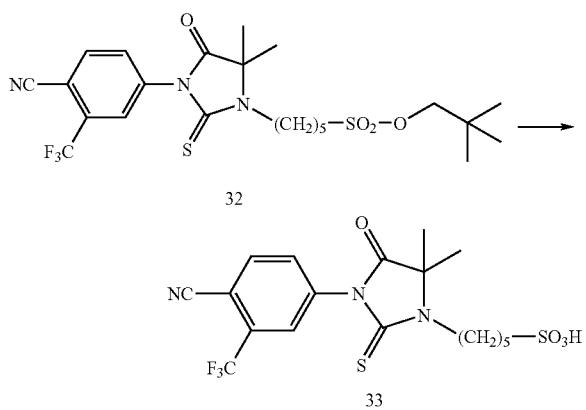

Compound 32 (460 mg) was dissolved in N,N-dimethylformamide. Then, tetramethylammonium chloride (472 mg) was added, and the mixture was heated to reflux for 6 hours. Following cooling, water was added, and an extraction was performed with dichloromethane. The organic layer washed with water and brine, and was dried over magnesium sulfate and then filtered. The solvent was distilled away under reduced pressure, and the resulting residue was then purified by silica gel column chromatography, to give 220 mg of the desired compound (compound 33) (yield: 55%).

$^1$H-NMR (300 MHz, CD$_3$OD) δ: 1.60-1.70 (2H, m), 1.72 (6H, s), 1.98-2.06 (4H, m), 2.97-3.02 (2H, m), 3.87-3.92 (2H, m), 8.05 (1H, dd, J=1.5, 8.2 Hz), 8.21 (1H, d, J=1.5 Hz), 8.26 (1H, d, J=8.2 Hz).

Rf value (silica gel plate, developing solvent: ethyl acetate:methanol=3:1):0.28.

MS (ESI): 464.5 ([M+H]$^+$).

(Fifth Step)

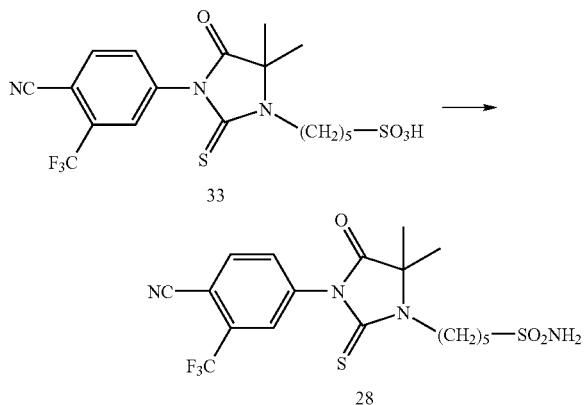

Triethylamine (2.4 mL) was added to compound 33 (80 mg), and the mixture was stirred for 1 hour at room temperature. The reaction mixture was then concentrated under reduced pressure to give triethylammonium salt of compound 33 (86 mg). In a separate vessel, triphenylphosphine (93 mg) was dissolved in dichloromethane; then, thionyl chloride (0.0205 mL) was added at 0° C. A dichloromethane solution of the abovementioned triethylammonium salt of compound 33 (54 mg) was added to this reaction solution at 0° C., and the resulting mixture was stirred for 4 hours at room temperature. A mixed solvent of pentane-diethyl ether (1:1, 5 mL) was added to the reaction solution, and the supernatant liquid was separated out and concentrated under reduced pressure. The residue thus obtained was dissolved in dichloromethane; then, aqueous ammonia (0.5 mL) was added at 0° C., and the resulting mixture was stirred for 1 hour at 0° C. Water was added, and an extraction was performed with dichloromethane. The organic layer was dried over magnesium sulfate, filtered, and concentrated. The resulting residue was purified by thin-layer chromatography (ethyl acetate:n-hexane=1:1) to give 7.6 mg of the desired compound (compound 28).

$^1$H-NMR (300 MHz, CDCl$_3$) δ: 1.50-1.60 (2H, m), 1.58 (6Hvs), 1.87-1.99 (4H, m), 3.15-3.21 (2H, m), 3.67-3.73 (2H, m), 4.61 (2H, brs), 7.77 (1H, dd, J=1.8, 8.1 Hz), 7.89 (1H, d, J=1.8 Hz), 7.95 (1H, d, J=8.1 Hz).

Rf value (silica gel plate, developing solvent: ethyl acetate:methanol=1:1):0.083.

MS (ESI): 463.7 ([M+H]$^+$).

Reference Example 5

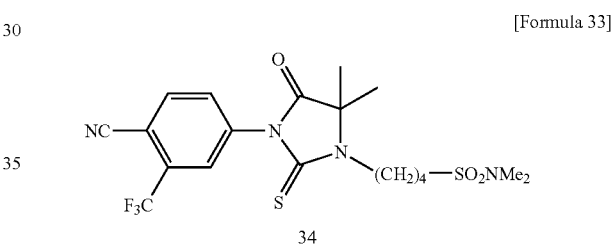

(First Step)

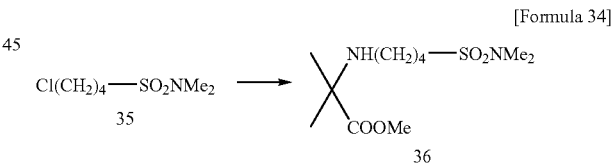

2-Aminoisobutyric acid methyl ester hydrochloride (1.0 g) and potassium carbonate (1.8 g) were dissolved in N,N-dimethylformamide (5 mL); then compound 35 (350 mg) and potassium iodide (50 mg) were added, and the resulting mixture was stirred for 36 hours at 80° C. Water was added, and an extraction was performed with ethyl acetate. The organic layer was dried over magnesium sulfate, filtered, and concentrated. The residue thus obtained was purified by silica gel column chromatography to give 119 mg of the desired compound (compound 36) (yield: 24%).

$^1$H-NMR (300 MHz, CDCl$_3$) δ: 1.29 (6H, s), 1.56-1.61 (2H, m), 1.83-1.89 (2H, m), 2.48 (2H, t, J=7.1 Hz), 2.87 (6H, s), 2.90-2.95 (2H, m), 3.70 (3H, s).

Rf value (silica gel plate, developing solvent: ethyl acetate:n-hexane 1:2):0.13.

(Second Step)

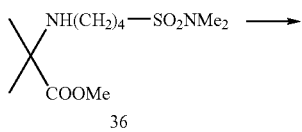

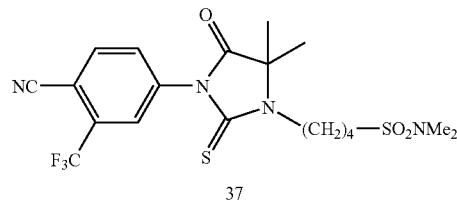

Compound 36 (115 mg) was dissolved in tetrahydrofuran (3 mL); then, 4-cyano-3-trifluoromethylphenyl isothiocyanate (125 mg) and triethylamine (2 drops) were added, and the resulting mixture was stirred for 3 hours at room temperature. The reaction solution was concentrated, and was then recrystallized using ethyl acetate:n-hexane=1:1 to give 98 mg of the desired compound (compound 37) (yield: 54%).

$^1$H-NMR (300 MHz, CD$_3$OD) δ: 1.50 (6H, s), 1.76-1.94 (4H, m), 2.77 (6H,), 3.00-3.05 (2H, m), 3.69-3.74 (2H, m), 7.81 (1H, dd, J=1.6, 8.4 Hz), 7.97 (1H, d, J=1.6 Hz), 8.02 (1H, d, J=8.4 Hz).

Rf value (silica gel plate, developing solvent: ethyl acetate: n-hexane=1:2):0.48.

MS (ESI): 477.5 ([M+H]$^+$).

Reference Example 6

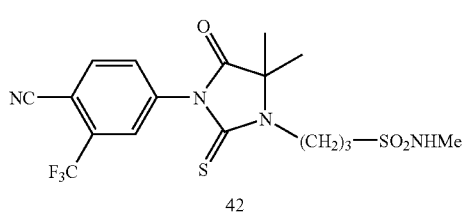

(First Step)

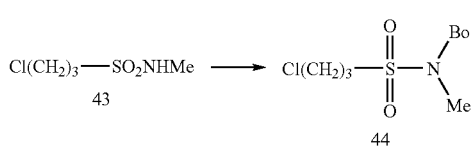

Compound 43 (1.08 g), di-t-butyl dicarbonate (2.06 g) and N,N-dimethylaminopyridine (77 mg) were dissolved in acetonitrile (12.6 mL), and this solution was stirred for 17 hours at room temperature. Water was added, and an extraction was performed with dichloromethane. The organic layer was dried over magnesium sulfate and filtered. Then, the solvent was distilled away under reduced pressure to give 1.65 g of the desired compound (compound 44) (yield: 96%).

$^1$H-NMR (300 MHz, CDCl$_3$) δ: 1.55 (9H, s), 2.23-2.32 (2H, m), 3.21 (3H, s), 3.62-3.69 (4H, m).

Rf value (silica gel plate, developing solvent: ethyl acetate: n-hexane=1:2):0.62.

(Second Step)

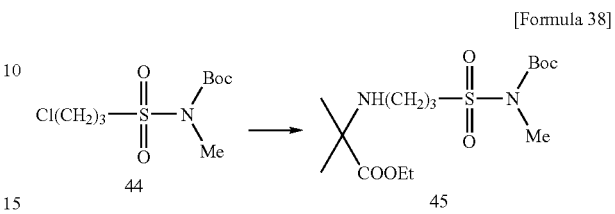

2-Aminoisobutyric acid ethyl ester hydrochloride (592 mg) and potassium carbonate (1.02 g) were dissolved in a mixed solvent of acetonitrile (5 mL) and dimethylformamide (1 mL), and the resulting mixture was stirred for 1 hour at room temperature. Compound 44 (800 mg) and sodium iodide (441 mg) were added, and the resulting mixture was stirred for 22 hours at 80 to 90° C. After the reaction solution was allowed to stand until cool, water was added, and an extraction was performed with ethyl acetate. The organic layer washed with brine, dried over magnesium sulfate and filtered. The solvent was then distilled away under reduced pressure, and the residue was purified by silica gel column chromatography (developing solvent: ethyl acetate:n-hexane=1:1) to give 813 mg of the desired compound (compound 45) (yield: 75%).

$^1$H-NMR (300 MHz, CDCl$_3$) δ: 1.27 (3H, t, J=7.1 Hz), 1.28 (6H, s), 1.54 (9H, s), 1.87-1.92 (2H, m), 2.59 (2H, t, J=6.5 Hz), 3.19 (3H, s), 3.54-3.59 (2H, m), 4.16 (2H, q, J=7.1 Hz).

Rf value (silica gel plate, developing solvent: ethyl acetate: n-hexane=1:1): 0.32.

(Third Step)

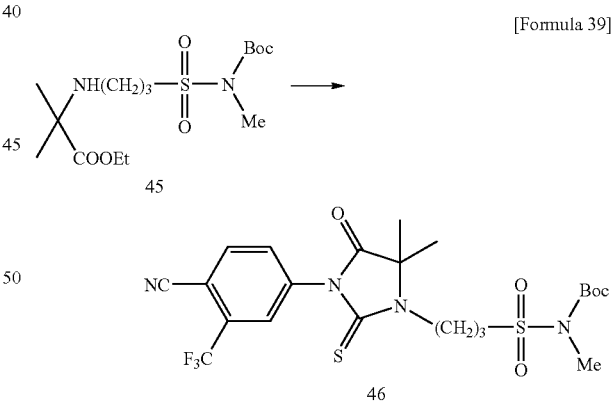

4-Cyano-3-trifluoromethylphenyl isothiocyanate (274 mg) was dissolved in tetrahydrofuran (5.5 mL); then, compound 45 (400 mg) and triethylamine (0.034 mL) were added, and the resulting mixture was stirred for 2 hours at room temperature. The reaction solution was concentrated under reduced pressure, and the resulting residue was purified by silica gel column chromatography (developing solvent: ethyl acetate:n-hexane=1:3) to give 624 mg of the desired compound (compound 46).

$^1$H-NMR (300 MHz, CDCl$_3$) δ: 1.54 (9H, s), 1.62 (6H, s), 2.35-2.40 (2H, m), 3.23 (3H, s), 3.60 (2H, t, J=7.1 Hz), 3.88-3.93 (2H, m), 7.77 (1H, dd, J=1.8, 8.1 Hz), 7.89 (1H, d, J=1.8 Hz), 7.96 (1H, d, J=8.1 Hz).

Rf value (silica gel plate, developing solvent: ethyl acetate: n-hexane=1:1):0.47.

(Fourth Step)

[Formula 40]

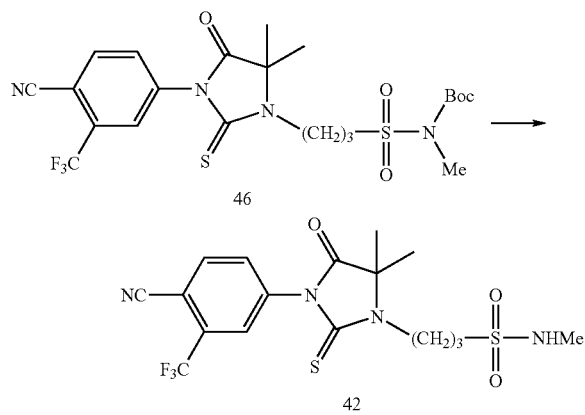

Compound 46 (300 mg) was dissolved in dichloromethane (2.7 mL), and this solution was cooled to 0° C. Trifluoroacetic acid (0.421 mL) was added dropwise, and the resulting mixture was stirred for 5.5 hours at room temperature. The reaction solution was purified by silica gel column chromatography (developing solvent: ethyl acetate n-hexane=1:1 or ethyl acetate:n-hexane:dichloromethane=1:1:1) to give 235 mg of the desired compound (compound 42) (yield: 96%).

$^1$H-NMR (300 MHz, CDCl$_3$) δ: 1.62 (6H, s), 2.33-2.39 (2H, m), 2.84 (3H, d, J=5.2 Hz), 3.16 (2H, t, J=7.1 Hz), 3.89-3.94 (2H, m), 4.35 (1H, q, J=5.2 Hz), 7.77 (1H, dd, J=1.7, 8.4 Hz), 7.90 (1H, d, J=1.7 Hz), 7.96 (1H, d, J=8.4 Hz).

Rf value (silica gel plate, developing solvent: ethyl acetate: n-hexane=1:1): 0.18.

MS (ESI$^-$): 447.1 ([M−H]$^-$).

Reference Example 7

[Formula 41]

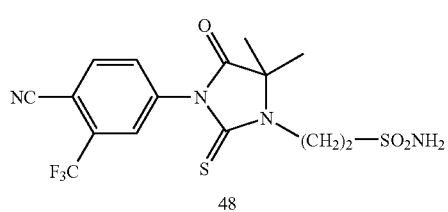

(First Step)

[Formula 42]

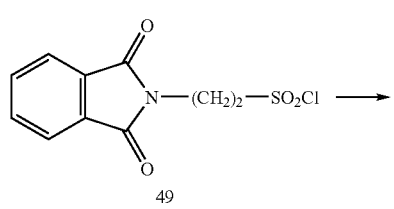

-continued

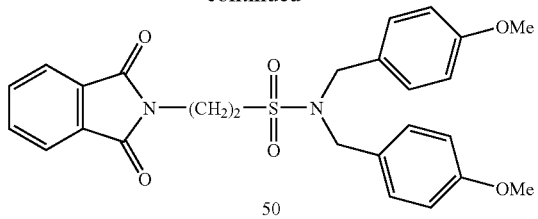

Bis(4-methoxybenzyl)amine (900 mg) was dissolved in dichloromethane (20 mL), and this solution was cooled to 0° C. Triethylamine (1.02 mL) was added, compound 49 (1.05 g) was added in small portions, and the resulting mixture was stirred for 3 hours at room temperature. Water was added to the reaction solution, and an extraction was performed with dichloromethane. The organic layer washed with brine, dried over magnesium sulfate, and filtered. The solvent was then distilled away under reduced pressure. The resulting residue was purified by silica gel column chromatography (developing solvent: ethyl acetate:n-hexane=1:1) to give 1.4 g of the desired compound (compound 50) (yield: 81%).

$^1$H-NMR (300 MHz, CDCl$_3$) δ: 3.24 (2H, t, J=6.8 Hz), 3.81 (6H, s), 4.10-4.14 (2H, m), 4.29 (4H, s), 6.88 (4H, d, J=8.7 Hz), 7.23 (4H, d, J=8.7 Hz), 7.73 (2H, dd, J=3.1, 5.3 Hz), 7.87 (2H, dd, J=3.1, 5.3 Hz).

Rf value (silica gel plate, developing solvent: ethyl acetate: n-hexane=1:1): 0.24.

(Second Step)

[Formula 43]

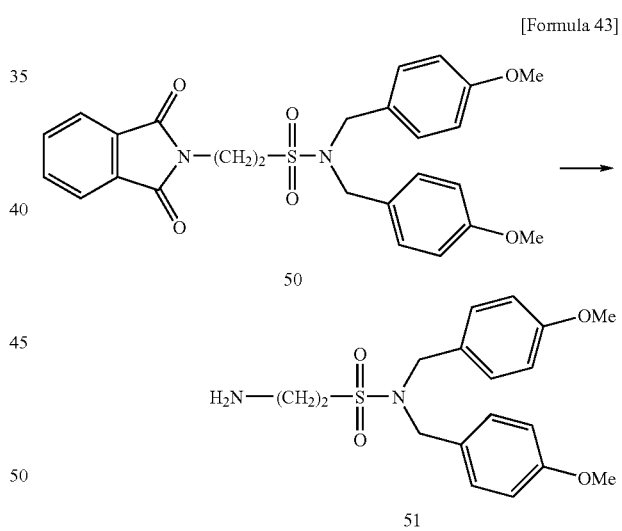

Compound 50 (1.4 g) was suspended in ethanol (15 mL); then, hydrazine monohydrate (0.151 mL) was added, and the resulting mixture was stirred overnight at room temperature. The reaction solution was filtered and the filtrate was concentrated under reduced pressure. The resulting residue was purified by silica gel column chromatography (developing solvent: dichloromethane methanol=100:1 to 50:1 to 20:1) to give 460 mg of the desired compound (compound 51) (yield: 45%).

$^1$H-NMR (300 MHz, CDCl$_3$) δ: 2.96 (2H, t, J=6.5 Hz), 3.16 (2H, t, J=6.5 Hz), 3.82 (6H, s), 4.27 (4H, s), 6.89 (4H, d, J=8.5 Hz), 7.22 (4H, d, J=8.5 Hz).

Rf value (silica gel plate, developing solvent: dichloromethane:methanol=10:1): 0.41.

(Third Step)

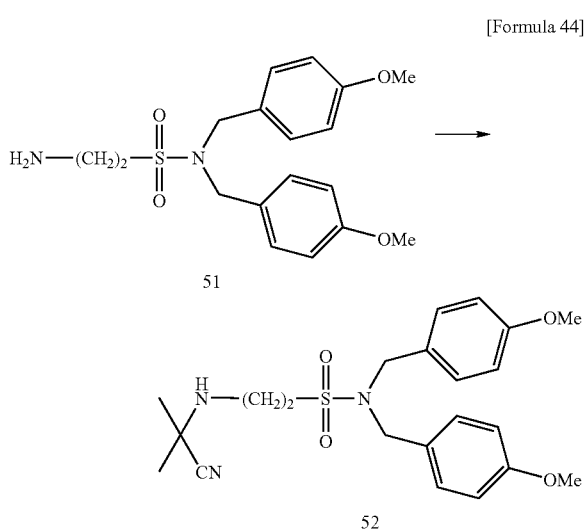

Compound 51 (450 mg) was dissolved in methanol (5 mL). Then, acetonecyanohydrin (0.136 mL) was added, and the resulting mixture was stirred overnight at room temperature. Next, acetonecyanohydrin (0.226 mL) was added, and the resulting mixture was stirred for 3 hours at 40 to 50° C. The reaction solution was concentrated under reduced pressure, and the resulting residue was purified by silica gel column chromatography (developing solvent: dichloromethane methanol=50:1) to give 330 mg of the desired compound (compound 52) (yield: 62%).

$^1$H-NMR (300 MHz, CDCl$_3$) δ: 1.44 (6H, s), 1.95 (1H, brs), 3.00-3.16 (4H, m), 3.82 (6H, s), 4.30 (4H, s), 6.89 (4H, d, J=8.7 Hz), 7.23 (4H, d, J=8.7 Hz).

Rf value (silica gel plate, developing solvent: dichloromethane:methanol=20:1): 0.67.

(Fourth Step)

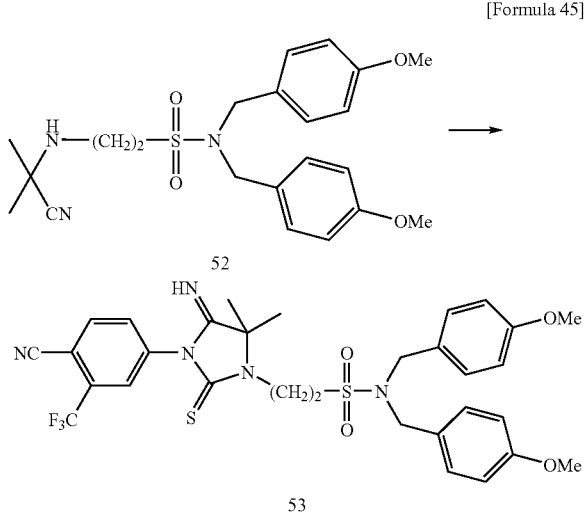

Compound 52 (220 mg) was dissolved in tetrahydrofuran (4.5 mL); then, triethylamine (0.014 mL) and 4-cyano-3-trifluoromethylphenyl isothiocyanate (116 mg) were added, and the resulting mixture was stirred for 3 hours at room temperature. The reaction solution was concentrated under reduced pressure, and the resulting residue was purified by silica gel column chromatography (developing solvent: dichloromethane:methanol=40:1) to give 259 mg of the desired compound (compound 53) (yield: 77%).

$^1$H-NMR (300 MHz, CDCl$_3$) δ: 1.55 (6H, s), 3.37-3.42 (2H, m), 3.81 (6H, s), 4.01-4.06 (2H, m), 4.29 (4H, s), 6.88 (4H, d, J=8.8 Hz), 7.25 (4H, d, J=8.8 Hz), 7.53-7.93 (4H, m).

Rf value (silica gel plate, developing solvent: dichloromethane:methanol=20:1): 0.24.

(Fifth Step)

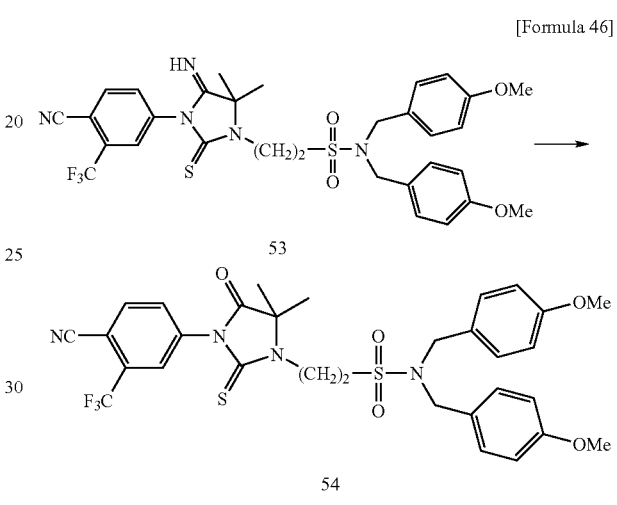

Compound 53 (259 mg) was dissolved in 1,4-dioxane (2.5 mL); then, 6 N—HCl (2.5 mL) was added, and the mixture was heated to reflux for 1 hour. After the mixture was allowed to stand until cool, water was added, and an extraction was performed with dichloromethane. The organic layer washed with brine, and was then dried over magnesium sulfate, filtered, and concentrated under reduced pressure. The resulting residue was purified by silica gel column chromatography (developing solvent: ethyl acetate:n-hexane=1:2 to 1:1) to give 144 mg of the desired compound (compound 54) (yield: 56%).

$^1$H-NMR (300 MHz, CDCl$_3$) δ: 1.54 (6H, s), 3.37-3.39 (2H, m), 3.81 (6H, s), 4.04-4.07 (2H, m), 4.30 (4H, s), 6.89 (4H, d, J=8.9 Hz), 7.25 (4H, d, J=8.9 Hz), 7.75 (1H, dd, J=8.5, 2.0 Hz), 7.88 (1H, d, J=2.0 Hz), 7.96 (1H, d, J=8.5 Hz).

Rf value (silica gel plate, developing solvent: ethyl acetate: n-hexane=1:1): 0.21.

(Sixth Step)

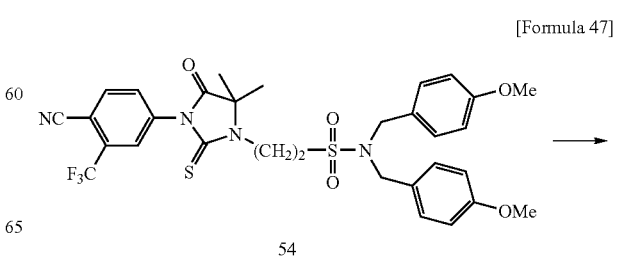

-continued

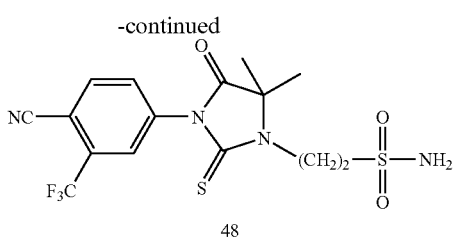

48

Compound 54 (140 mg), trifluoroacetic acid (1 mL) and anisole (0.02 mL) were mixed; this mixture was stirred for 2 hours at room temperature, and was then heated to reflux for 1 hour. After the reaction mixture was allowed to stand until cool, water was added, and an extraction was performed with ethyl acetate. The organic layer washed with brine, and was then dried over magnesium sulfate, filtered, and concentrated under reduced pressure. The resulting residue was purified by silica gel column chromatography (developing solvent: ethyl acetate:n-hexane=1:1 to 2:1 to 4:1) to give 64 mg of the desired compound (compound 48) (yield: 72%).

$^1$H-NMR (300 MHz, CDCl$_3$) δ: 1.64 (6H, s), 3.67-3.72 (2H, m), 4.17-4.22 (2H, m), 4.88 (2H, brs), 7.76 (1H, dd, J=1.8, 8.5 Hz), 7.88 (1H, d, J=1.8 Hz), 7.97 (1H, d, J=8.5 Hz).

Rf value (silica gel plate, developing solvent: ethyl acetate: n-hexane=3:1): 0.21.

MS (ESI$^-$): 419.1 ([M−H]$^-$).

Example 1

[Formula 48]

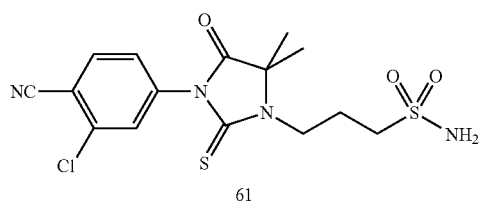

61

(First Step)

[Formula 49]

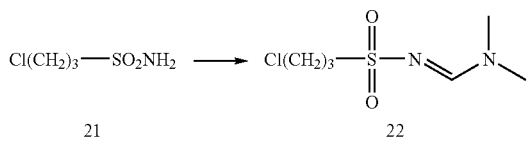

Compound 21 (4.0 g) was dissolved in N,N-dimethylformamide (20 mL); then, N,N-dimethylformamide dimethyacetal (3.7 mL) was added, and the resulting mixture was stirred for 1 hour at room temperature. Ethyl acetate was added, and the organic layer washed with water, dried over magnesium sulfate, and filtered. The solvent was then distilled away under reduced pressure to give 3.05 g of the desired compound (compound 22) (yield: 57%).

$^1$H-NMR (300 MHz, CDCl$_3$) δ: 2.25-2.34 (2H, m), 3.05 (3H, s), 3.15 (3H, s), 3.18 (2H, t, J=7.2 Hz), 3.71 (2H, t, J=6.0 Hz), 8.05 (1H, s).

Rf value (silica gel plate, developing solvent: ethyl acetate: n-hexane=2:1): 0.31.

(Second Step)

[Formula 50]

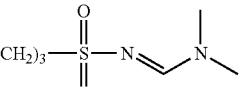

Under a nitrogen atmosphere, 2-aminoisobutyric acid ethyl ester hydrochloride (20.84 g) was dissolved in N,N-dimethylformamide (40 mL); then, potassium carbonate (34.37 g) was added, and the resulting mixture was stirred for 30 minutes. A solution prepared by dissolving compound 22 (8.82 g) in N,N-dimethylformamide (19 mL) was added at room temperature; then, sodium iodide (6.21 g) was further added, and the resulting mixture was heated to reflux for 15 hours at 80 to 90° C. This solution was concentrated under reduced pressure to remove the N,N-dimethylformamide. Water was added, and an extraction was performed twice with ethyl acetate; the extract was then dried over magnesium sulfate and filtered. The residue obtained by concentrating the filtrate under reduced pressure was purified by silica gel column chromatography (NH-Silicagel, ethyl acetate:hexane=1: 1) to give 9.27 g of the desired compound (compound 59) (yield: 73%).

$^1$H-NMR (400 MHz, CDCl$_3$) δ: 1.27 (3H, t, J=7.3 Hz), 1.28 (6H, s), 1.88-1.95 (2H, m), 2.58 (2H, t, J=6.8 Hz), 3.04 (3H, s), 3.08-3.12 (2H, m), 3.12 (3H, s), 4.15 (2H, q, J=7.3 Hz), 8.02 (1H, s).

MS (ESI): 330.2 ([M+Na]$^+$)

(Third Step)

[Formula 51]

58

Compound 58 (63.3 mg), compound 59 (100 mg) and dimethylaminopyridine (60.4 mg) were dissolved in tetrahydrofuran (0.7 mL), and this solution was stirred for 45 minutes at 60° C. under a nitrogen atmosphere. Water was added to the reaction solution, and an extraction was performed with dichloromethane. The organic layer was dried over sodium sulfate, filtered, and concentrated under reduced pressure. The resulting residue was purified by silica gel column chromatography (developing solvent: dichlormethane:methanol=20:1) to give 135.5 mg of the desired compound (compound 60) (yield: 91%).

¹H-NMR (400 MHz, CDCl₃) δ: 1.60 (6H, s), 2.32-2.38 (2H, m), 3.06 (3H, s), 3.13 (2H, t, J=6.6 Hz), 3.16 (3H, s), 3.93-3.95 (2H, m), 7.44 (1H, dd, J=1.5, 8.4 Hz), 7.60 (1H, d, J=1.5 Hz), 7.78 (1H, d, J=8.4 Hz), 8.07 (1H, s).

MS (ESI): 455.9 ([M+H]⁺).

(Fourth Step)

[Formula 52]

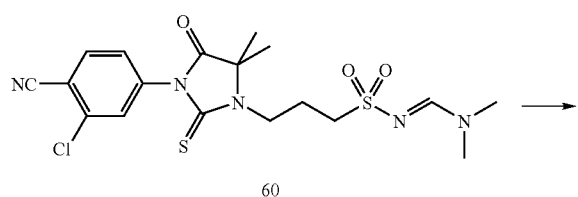
60

→

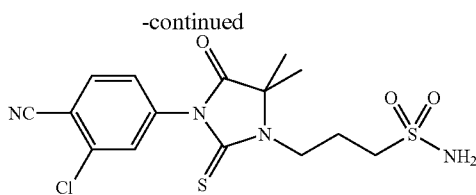
61

Compound 60 (135.5 mg) was dissolved in 1,4-dioxane (2.4 mL); then, 6 N HCl (1.2 mL) was added, and the resulting mixture was stirred for 2 hours at 80° C. After the reaction mixture was allowed to stand until cool, water was added at 0° C., and an extraction was performed with dichloromethane. The organic layer washed with water and brine, and was then dried over sodium sulfate, filtered, and concentrated under reduced pressure. The resulting residue was purified by silica gel column chromatography (developing solvent: dichloromethane:methanol=30:1) to give 103.8 mg of the desired compound (compound 61) (yield: 86%).

¹H-NMR (400 MHz, DMSO-d₆) δ: 1.53 (6H, s), 2.12-2.22 (2H, m), 3.10 (2H, t, J=7.3 Hz), 3.81 (2H, t, J=7.3 Hz), 6.86 (2H, s), 7.65 (1H, d, J=8.1 Hz), 7.96 (1H, s), 8.15 (1H, d, J=8.4 Hz).

MS (ESI): 400.9 ([M+H]⁺).

The following compounds were synthesized by the method as in Example 1.

TABLE 1-1

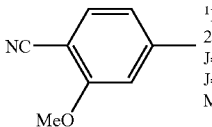
67

| Example No. | Q | Data |
|---|---|---|
| 2 | 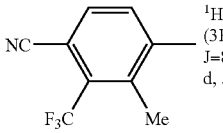 | ¹H-NMR(400 MHz, DMSO-d₆) δ: 1.54(6H, s), 2.12-2.25(2H, m), 3.08-3.17(2H, m), 3.82(2H, t, J=7.7 Hz), 3.91(3H, s), 6.87(2H, s), 7.14(1H, d, J=8.1 Hz), 7.36(1H, s), 7.87(1H, d, J=8.1 Hz) MS(ESI): 397.0([M + H]⁺) |
| 3 | 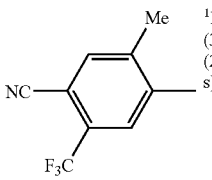 | ¹H-NMR(400 MHz, DMSO-d₆) δ: 1.56(3H, s), 1.58 (3H, s), 2.15-2.20(2H, m), 2.23(3H, s), 3.10(2H, t, J=8.1 Hz), 3.78-3.90(2H, m), 6.87(2H, s), 8.00(1H, d, J=8.1 Hz), 8.18(1H, d, J=8.1 Hz) |
| 4 |  | ¹H-NMR(400 MHz, DMSO-d₆) δ: 1.54(3H, s), 1.58 (3H, s), 2.12-2.25(2H, m), 2.22(3H, s), 3.05-3.15 (2H, m), 3.75-3.90(2H, m), 6.87(2H, s), 8.22(1H, s), 8.30(1H, s) |

TABLE 1-1-continued

67

[Structure: hydantoin with N-Q, gem-dimethyl, and N-propyl-sulfonamide substituents]

| Example No. | Q | Data |
|---|---|---|
| 5 | 4-nitro-3-(trifluoromethyl)phenyl (O₂N-, F₃C-) | Rf: 0.29(Ethyl acetate)<br>MS(ESI⁻): 453([M − H]⁻) |
| 6 | 4-cyano-3-methylphenyl (NC-, Me-) | Rf: 0.40(Ethyl acetate)<br>MS(ESI⁻): 379([M − H]⁻) |
| 7 | 4-cyano-3-ethylphenyl (NC-, Et-) | MS(ESI): 395.0([M + H]⁺) |
| 8 | 4-nitro-3-methylphenyl (O₂N-, Me-) | Rf: 0.40(Ethyl acetate)<br>MS(ESI⁻): 399([M − H]⁻) |
| 9 | 4-(trifluoromethyl)naphthalen-1-yl (F₃C-) | Rf: 0.20(Ethyl acetate:n-Hexane = 1:1)<br>MS(ESI⁻): 458([M − H]⁻) |

TABLE 1-2

| | | |
|---|---|---|
| 10 | 4-cyanophenyl (NC-) | ¹H-NMR(270 MHz, CDCl₃) δ : 1.60(6H, s), 2.35-2.48 (2H, m), 3.28(2H, t, J=7.0 Hz), 3.88-3.98(2H, m), 4.70(2H, brs), 7.51(2H, d, J=8.4 Hz), 7.79(2H, d, J=8.4 Hz)<br>MS(ESI): 366.9([M + H]⁺) |
| 11 | 4-carboxyphenyl (HOOC-) | Rf: 0.42(Ethyl acetate, developed twice)<br>MS(ESI⁻): 384([M − H]⁻) |
| 12 | 4-carbamoylphenyl (H₂N-C(=O)-) | Rf: 0.57(Ethyl acetate:Methanol = 3:1)<br>MS(ESI): 385([M + H]⁺) |
| 13 | 4-(dimethylcarbamoyl)phenyl (Me₂N-C(=O)-) | Rf: 0.70(Ethyl acetate:Methanol = 3:1)<br>MS(ESI): 413([M + H]⁺) |

TABLE 1-2-continued

| 14 | [structure: benzoic acid with CF3] | Rf: 0.067(Ethyl acetate)<br>MS(ESI): 454.0([M + H]+) |
| --- | --- | --- |
| 15 | [structure: benzamide with CF3] | Rf: 0.34(Ethyl acetate)<br>MS(ESI): 452.9([M + H]+) |
| 16 | [structure: N,N-dimethyl benzamide with CF3] | Rf: 0.28(Ethyl acetate)<br>MS(ESI): 481.1([M + H]+) |
| 17 | [structure: cyanonaphthalene] | Rf: 0.60(Ethyl acetate)<br>MS(ESI−): 415([M − H]−) |
| 18 | [structure: nitronaphthalene] | Rf: 0.20(Dichloromethane:Methanol = 30:1)<br>MS(ESI−): 435([M − H]−) |
| 19 | [structure: naphthalene carboxamide] | Rf: 0.30(Dichloromethane:Methanol = 15:1)<br>MS(ESI): 435([M − H]−) |
| 20 | [structure: N,N-dimethyl naphthalene carboxamide] | Rf: 0.09(Dichloromethane:Methanol = 30:1)<br>MS(ESI): 463([M + H]+) |

Example 21

[Formula 53]

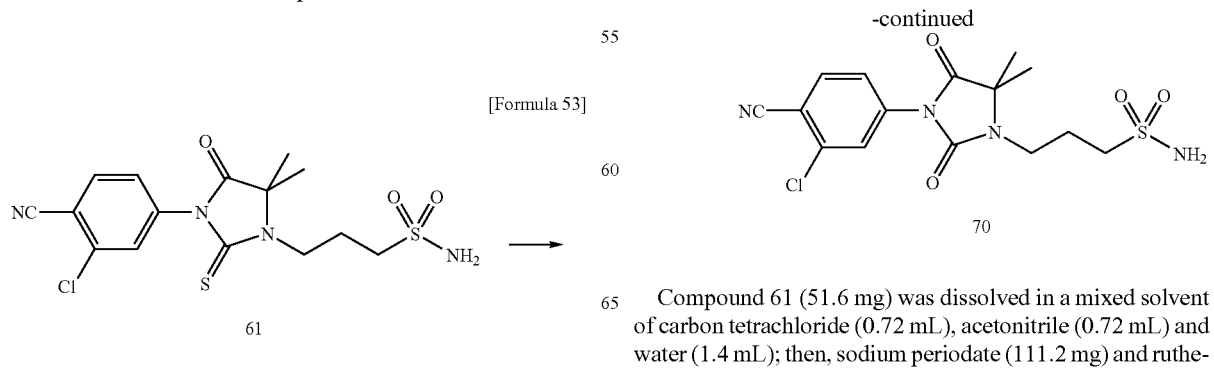

Compound 61 (51.6 mg) was dissolved in a mixed solvent of carbon tetrachloride (0.72 mL), acetonitrile (0.72 mL) and water (1.4 mL); then, sodium periodate (111.2 mg) and ruthenium (III) chloride n hydrate (1.3 mg) were added, and the resulting mixture was stirred for 3 hours at room temperature. Water was added to the reaction solution, and an extraction was performed with dichloromethane; then, the organic layer was dried over sodium sulfate, filtered, and concentrated under reduced pressure. The resulting residue was purified by thin-layer chromatography (silica gel plate, developing solvent: dichloromethane:methanol=20:1) to give 37.1 mg of the desired compound (compound 70) (yield: 74%).

$^1$H-NMR (400 MHz, DMSO-$d_6$) δ: 1.46 (6H, s), 1.98-2.05 (2H, m), 3.05-3.10 (2H, m), 3.40-3.50 (2H, m), 6.82 (2H, s), 7.70 (1H, dd, J=1.5, 8.8 Hz), 7.91 (1H, d, J=1.5 Hz), 8.12 (1H, d, J=8.8 Hz).

MS (ESI): 790.6 ([2M+Na]$^+$).

The following compounds were synthesized by the same method as in Example 21.

(First Step)

[Formula 55]

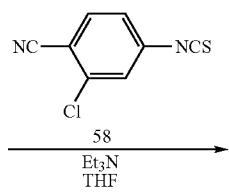

TABLE 2

71

| Example No. | Q | Data |
|---|---|---|
| 22 | NC—⟨benzene ring with MeO⟩— | $^1$H-NMR(400 MHz, DMSO-$d_6$) δ: 1.46(6H, s), 1.98-2.08(2H, m), 3.06-3.10(2H, m), 3.45(2H, t, J=7.3 Hz), 3.91(3H, s), 6.83(2H, s), 7.20(1H, dd, J=1.1,8.1 Hz), 7.36(1H, s), 7.85(1H, d, J=8.1 Hz) MS(ESI): 381.0([M + H]$^+$) |
| 23 | NC—⟨benzene ring with F$_3$C and Me⟩— | $^1$H-NMR(400 MHz, DMSO-$d_6$) δ: 1.50(3H, s), 1.51(3H, s), 2.00-2.10(2H, m), 2.27(3H, s), 3.02-3.12(2H, m), 3.46(2H, t, J=8.8 Hz), 6.84(2H, s), 7.94(1H, d, J=8.4 Hz), 8.16(1H, d, J=8.1 Hz) |
| 24 | NC—⟨benzene ring with Me and F$_3$C⟩— | $^1$H-NMR(400 MHz, DMSO-$d_6$) δ: 1.49(3H, s), 1.51 (3H, s), 1.99-2.13(2H, m), 2.26(3H, s), 3.02-3.15 (2H, m), 3.40-3.50(2H, m), 6.84(2H, s), 8.13(1H, s), 8.27(1H, s) |

Example 25

50

[Formula 54]

-continued

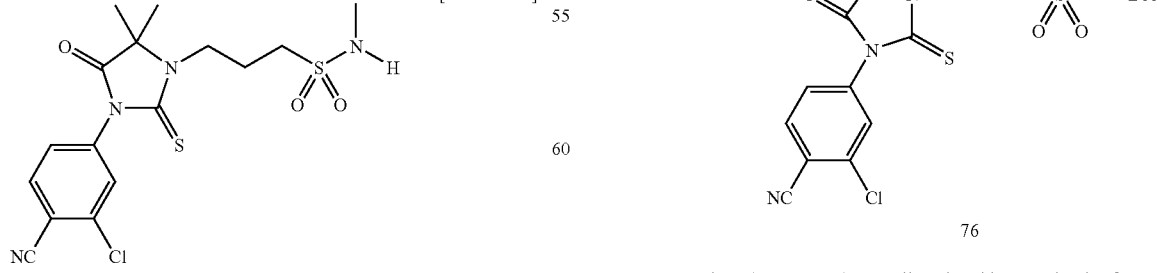

Compound 45 (170.7 mg) was dissolved in tetrahydrofuran (1.7 mL); then, compound 58 (100 mg) and triethylamine (0.013 mL) were added, and the mixture was heated to reflux for 1.5 hours. After the reaction mixture was allowed to stand until cool, water was added, and an extraction was performed with ethyl acetate. The organic layer washed with an aqueous solution of citric acid, a saturated aqueous solution of sodium hydrogencarbonate, and brine, and was then dried over magnesium sulfate, filtered, and concentrated under reduced pressure. The resulting residue was purified by silica gel column chromatography (developing solvent: hexane:ethyl acetate=1:1) to give 223 mg of the desired compound (compound 76) (yield: 93%).

$^1$H-NMR (400 MHz, CDCl$_3$): 1.54 (9H, s), 1.59 (6H, s), 2.33-2.40 (2H, m), 3.22 (3H, s), 3.60 (2H, t, J=7.0 Hz), 3.89 (2H, t, J=8.0 Hz), 7.44 (1H, d, J=8.4 Hz), 7.61 (1H, s), 7.79 (1H, d, J=8.4 Hz).

MS (ESI): 458.9 ([M+H−57]$^+$).

(Second Step)

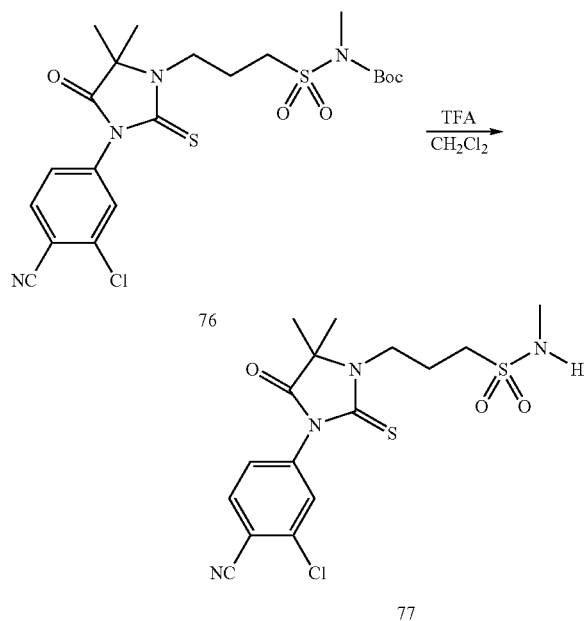

[Formula 56]

144.1 mg of the desired compound (compound 77) (yield: 81%) was obtained by the same method as in the fourth step of Reference Example 6.

$^1$H-NMR (400 MHz, CDCl$_3$): 1.60 (6H, s), 2.33-2.38 (2H, m), 2.85 (3H, d, J=5.1 Hz), 3.16 (2H, t, J=6.8 Hz), 3.91 (2H, t, J=8.4 Hz), 4.20-4.28 (1H, m), 7.44 (1H, d, J=8.4 Hz), 7.61 (1H, s), 7.79 (1H, d, J=8.1 Hz).

MS (ESI): 414.9 ([M+H]$^+$).

Example 26

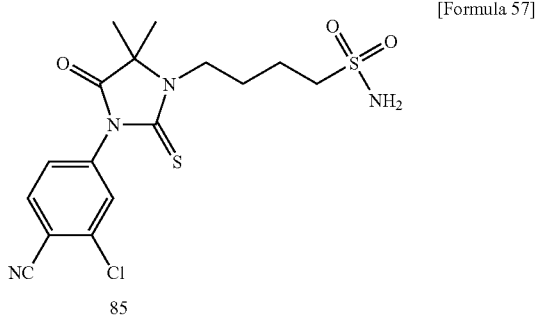

[Formula 57]

(First Step)

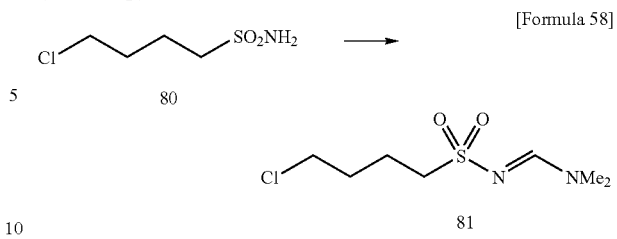

[Formula 58]

3.60 g of the desired compound (compound 81) (yield: 85%) was obtained by the same method as in the first step of Example 1.

$^1$H-NMR (270 MHz, CDCl$_3$): 1.88-2.05 (4H, m), 3.00-3.08 (5H, m), 3.14 (3H, s), 3.57 (2H, t, J=5.8 Hz), 8.04 (1H, s).

Rf value (silica gel plate, developing solvent: ethyl acetate): 0.34.

(Second Step)

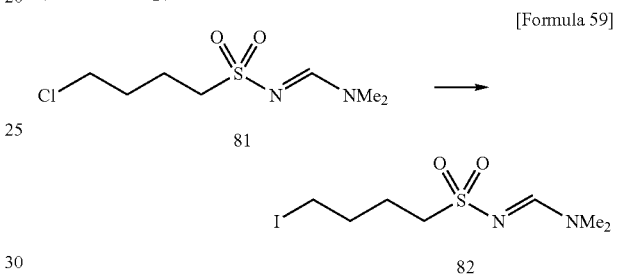

[Formula 59]

Compound 81 (3.70 g) was dissolved in acetone (80 mL); then, sodium iodide (24.5 g) was added, and the resulting mixture was heated to reflux for 12 hours. After allowed to stand until cool, the reaction solution was concentrated under reduced pressure; then, water was added, and an extraction was performed with ethyl acetate. The organic layer washed with a 5% aqueous solution of sodium thiosulfate, and was then dried over magnesium sulfate, filtered, and concentrated under reduced pressure to give 3.51 g of the desired compound (compound 82) (yield: 68%).

$^1$H-NMR (270 MHz, CDCl$_3$): 1.86-2.08 (4H, m), 3.03 (2H, t, J=6.9 Hz), 3.06 (3H, s), 3.15 (3H, s), 3.20 (2H, t, J=6.3 Hz), 8.04 (1H, s).

Rf value (silica gel plate, developing solvent: ethyl acetate): 0.38.

(Third Step)

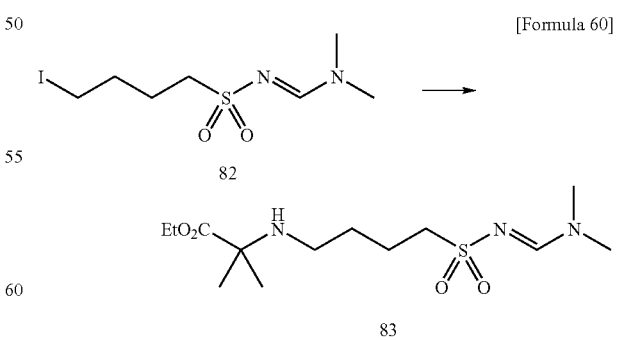

[Formula 60]

2-Aminoisobutyric acid ethyl ester hydrochloride (409 mg) was dissolved in N,N-dimethylformamide (5 mL); then, potassium carbonate (868 mg) was added, and the resulting mixture was stirred for 30 minutes at room temperature. Next, compound 82 (1.0 g) was added, and the resulting mixture was heated to reflux for 5 hours at 80 to 90° C. After allowed to stand until cool, the reaction mixture was concentrated under reduced pressure. The resulting residue was then purified by silica gel column chromatography (developing solvent: dichloromethane:methanol=1:0 to 5:1) to give 976.4 mg of the desired compound (compound 83) (yield: 97%).

MS (ESI): 322.2 ([M+H]$^+$).

Rf value (silica gel plate, developing solvent: dichloromethane:methanol=5:1): 0.20.

(Fourth Step)

[Formula 61]

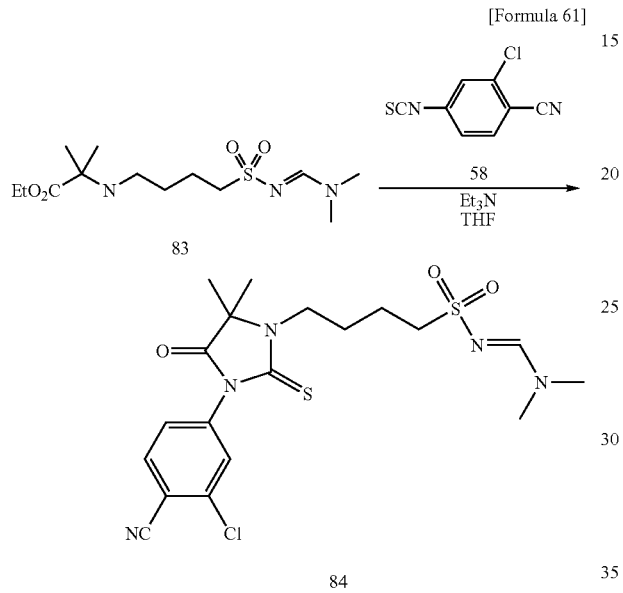

Compound 83 (75.1 mg) was dissolved in tetrahydrofuran (0.75 mL); then, compound 58 (50 mg) and triethylamine (0.0065 mL) were added, and the resulting mixture was heated to reflux for 1.5 hours. Water was added to the reaction solution, and an extraction was performed with ethyl acetate. The organic layer washed with brine, and was then dried over magnesium sulfate, filtered, and concentrated under reduced pressure. The resulting residue was purified by silica gel column chromatography (developing solution: hexane:ethyl acetate=1:0 to 0:1) to give 28.6 mg of the desired compound (compound 84) (yield: 26%).

MS (ESI): 470.0 ([M+H]$^+$).

Rf value (silica gel plate, developing solvent: ethyl acetate): 0.30.

(Fifth Step)

[Formula 62]

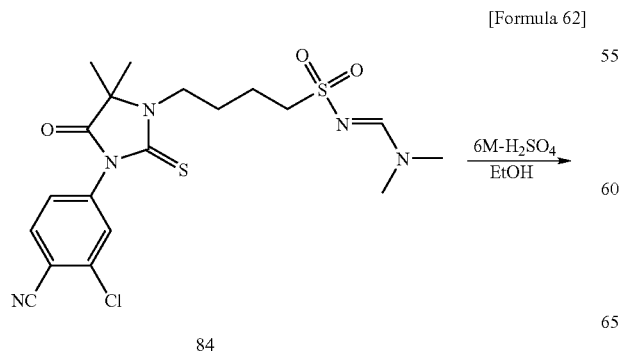

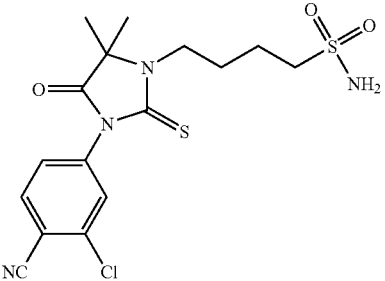

Compound 84 (81 mg) was dissolved in ethanol (0.54 mL); then, 6 M sulfuric acid (0.27 mL) was added, and the resulting mixture was stirred for 2 hours at 90° C. After the reaction mixture was allowed to stand until cool, the precipitated solid was collected by filtration to give 44.7 mg of the desired compound (compound 85) (yield: 43%).

$^1$H-NMR (400 MHz, DMSO-d$_6$): 1.54 (6H, s), 1.72-1.92 (4H, m), 3.06 (2H, t, J=8.4 Hz), 3.72 (2H, t, J=8.1 Hz), 6.80 (2H, s), 7.66 (1H, d, J=8.4 Hz), 7.97 (1H, s), 8.16 (1H, d, J=8.4 Hz).

MS (ESI): 415.0 ([M+H]$^+$).

Example 27

[Formula 63]

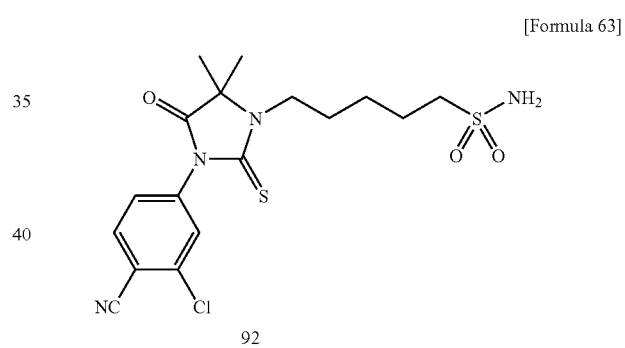

(First Step)

[Formula 64]

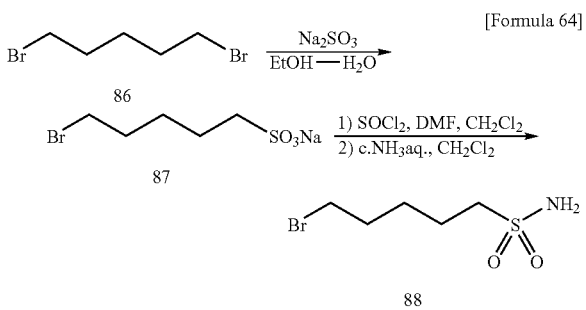

Compound 86 (25.0 g) was dissolved in ethanol (100 mL); then, a solution prepared by dissolving sodium sulfite (8.24 g) in water (50 mL) was added at 100° C., and the resulting mixture was stirred for 1 hour at 100° C. After allowed to stand until cool, the reaction solution washed with dichloromethane, and the water layer was concentrated under reduced pressure to give a crude product of compound 87 (17.76 g). This crude product was suspended in dichloromethane (80 mL); then, thionyl chloride (45 mL) and N,N-dimethylformamide (0.5 mL) were added, and the resulting mixture was stirred for 4 hours at 60° C. After allowed to stand until cool, the reaction solution was filtered, and the filtrate was concentrated under reduced pressure. The residue thus obtained (17.5 g) was dissolved in dichloromethane (120 mL); then, aqueous ammonia (16 mL) was added at 0° C., and the resulting mixture was stirred for 30 minutes. Next, water was added, and an extraction was performed with dichloromethane. The organic layer washed with brine, and was then dried over magnesium sulfate, filtered, and concentrated under reduced pressure. The resulting residue was purified by silica gel column chromatography (developing solvent: hexane:ethyl acetate=1:0 to 1:1) to give 1.97 g of the desired compound (compound 88) (yield: 16%).

$^1$H-NMR (400 MHz, CDCl$_3$): 1.59-1.66 (2H, m), 1.82-1.95 (4H, m), 3.14 (2H, t, J=7.7 Hz), 3.43 (2H, t, J=6.6 Hz), 4.52 (2H, brs).

Rf value (silica gel plate, developing solvent: hexane:ethyl acetate=1:1): 0.36.

(Second Step)

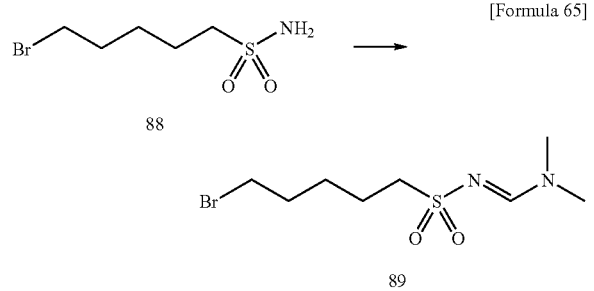

[Formula 65]

Compound 88 (1.97 g) was dissolved in ethyl acetate (10 mL); then N,N-dimethylformamide dimethylacetal (1.25 mL) was added, and the resulting mixture was stirred for 1 hour at room temperature. Next, ethyl acetate was added, and the organic layer washed with brine, dried over magnesium sulfate, and filtered. The solvent was distilled away under reduced pressure, and the resulting residue was purified by silica gel column chromatography (developing solvent: hexane:ethyl acetate=1:0 to 1:1) to give 2.07 g of the desired compound (compound 89) (yield: 85%).

MS (ESI): 285.1 ([M+H]$^+$).

Rf value (silica gel plate, developing solvent: hexane:ethyl acetate=1:1): 0.15.

(Third Step)

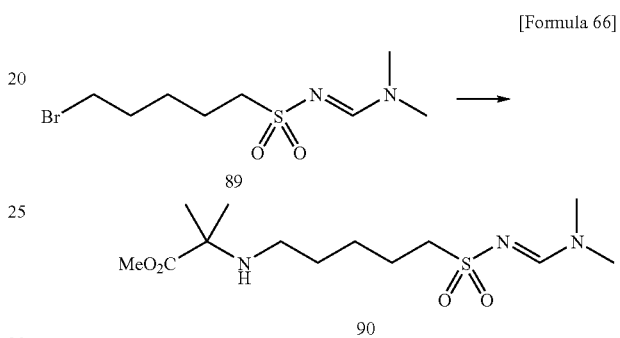

[Formula 66]

554.6 mg of the desired compound (compound 90) (yield: 49%) was obtained by the same method as in the second step of Example 1.

MS (ESI) 322.2 ([M+H]$^+$).

Rf value (silica gel plate, developing solvent: dichloromethane:methanol=10:1): 0.46.

(Fourth Step)

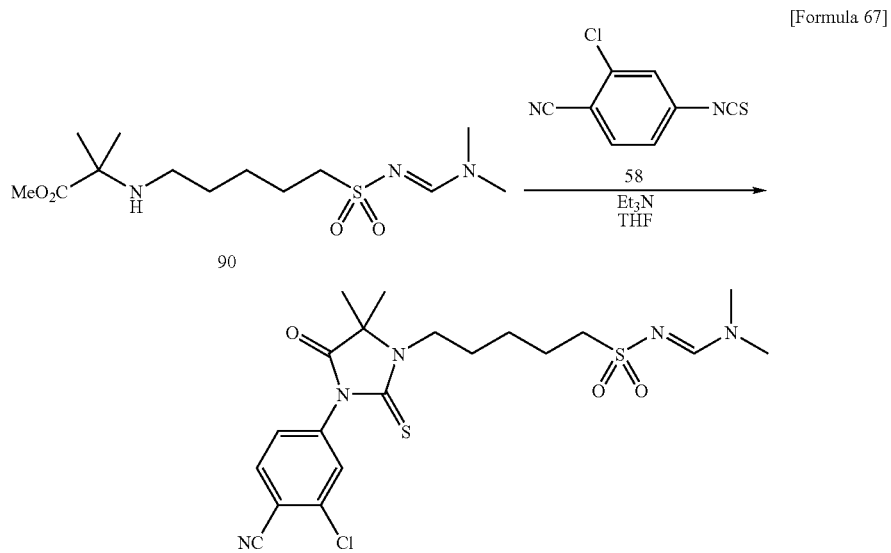

[Formula 67]

Compound 90 (100 mg) was dissolved in tetrahydrofuran (1 mL); then, compound 58 (66.6 mg) and triethylamine (0.009 mL) were added, and the resulting mixture was heated to reflux for 1 hour. After the reaction mixture was allowed to stand until cool, water was added, and an extraction was performed with ethyl acetate. The organic layer washed with brine, and was then dried over magnesium sulfate, filtered, and concentrated under reduced pressure. The resulting residue was purified by silica gel column chromatography (developing solvent:hexane:ethyl acetate=1:0 to 0:1) to give 151 mg of the desired compound (compound 91) (yield: 99%).

MS (ESI): 484.1 ([M+H]$^+$).

Rf value (silica gel plate, developing solvent: ethyl acetate): 0.27.

(Fifth Step)

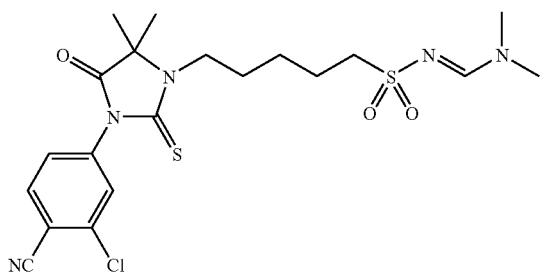

91

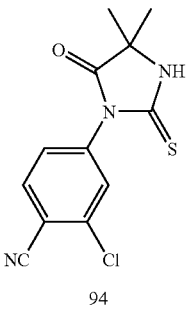

94

[Formula 68]

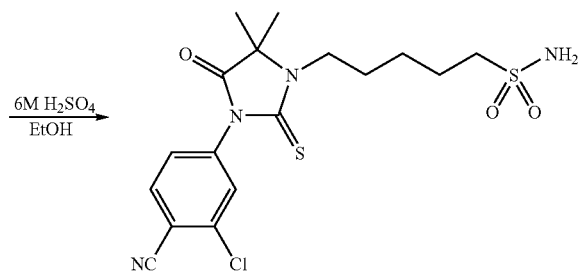

92

113.2 mg of the desired compound (compound 92) (yield: 85%) was obtained by the same method as in the fifth step of Example 26.

$^1$H-NMR (400 MHz, CDCl$_3$): 1.50-1.63 (2H, m), 1.85-1.99 (4H, m), 3.18 (2H, t, J=7.7 Hz), 3.69 (2H, t, J=8.1 Hz), 4.55 (2H, brs), 7.45 (1H, split d, J=8.4 Hz), 7.61 (1H, split s), 7.78 (1H, d, J=8.4 Hz).

MS (ESI): 429.1 ([M+H]$^+$).

Rf value (silica gel plate, developing solvent: ethyl acetate): 0.53.

1.014 g of the desired compound (compound 94) (yield: 61%) was obtained by the same method as in the fourth step of Example 27.

$^1$H-NMR (400 MHz, CDCl$_3$): 1.60 (6H, s), 7.46 (1H, d, J=8.1 Hz), 7.62 (1H, s), 7.79 (1H, d, J=8.1 Hz), 7.93 (1H, brs).

Rf value (silica gel plate, developing solvent: hexane:ethyl acetate=1:1): 0.35.

(Second Step)

[Formula 71]

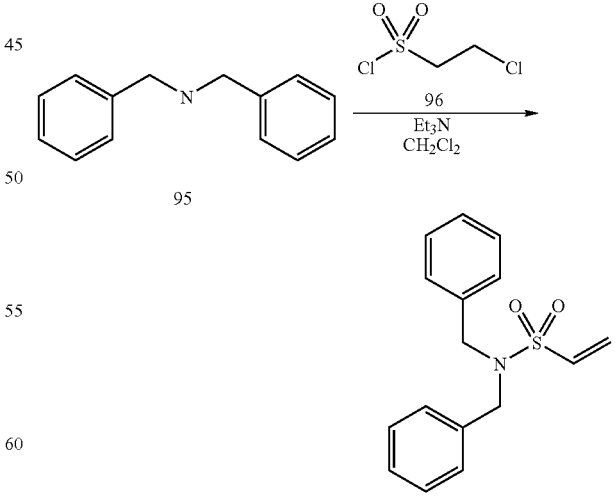

97

Example 28

[Formula 69]

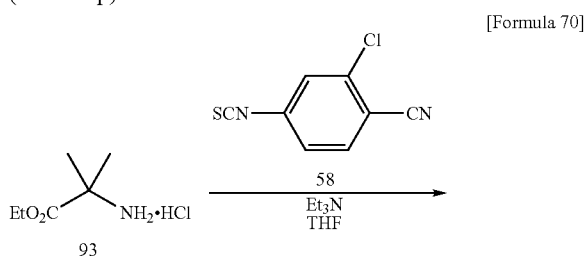

99

(First Step)

[Formula 70]

Compound 96 (0.795 mL) was dissolved in dichloromethane (10 mL); then, compound 95 (1.0 g) was added at 0° C. under a nitrogen atmosphere, and a solution prepared by dissolving triethylamine (2.83 mL) in dichloromethane (10 mL) was further added dropwise. The reaction solution was stirred overnight at room temperature. A 1 N aqueous solution of sodium carbonate was added to the reaction solution, and an extraction was performed with dichloromethane. The organic layer was concentrated under reduced pressure, and the resulting residue was then purified by silica gel column chromatography (developing solvent: hexane:ethyl acetate=1:0 to 4:1) to give 991.6 mg of the desired compound (compound 97) (yield: 68%).

MS (ESI): 287.8 ([M+H]$^+$).

Rf value (silica gel plate, developing solvent: ethyl acetate: hexane=4:1):0.27.

(Third Step)

[Formula 72]

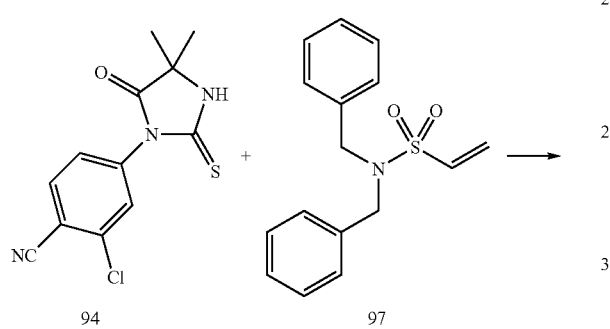

Compound 97 (100 mg) was dissolved in 1,3-dimethyl-2-imidazolidinone (3 mL); then, compound 94 (97.4 mg) and potassium carbonate (52.9 mg) were added, and the resulting mixture was stirred for 7 hours at 100° C. After the reaction mixture was allowed to stand until cool, water was added, and an extraction was performed with ethyl acetate. The organic layer washed with water and brine, dried over magnesium sulfate, filtered, and concentrated under reduced pressure. The resulting residue was purified by silica gel column chromatography (developing solvent:hexane:ethyl acetate=1:0 to 2:1) to give 74.6 mg of the desired compound (compound 98) (yield: 38%).

$^1$H-NMR (400 MHz, CDCl$_3$): 1.54 (6H, s), 3.41 (2H, t, J=7.7 Hz), 4.07 (2H, t, J=7.5 Hz), 4.38 (4H, s), 7.30-7.39 (10H, m), 7.42 (1H, d, J=8.1 Hz), 7.58 (1H, s), 7.79 (1H, d, J=8.1 Hz).

MS (ESI): 566.9 ([M+H]$^+$).

(Fourth Step)

[Formual 73]

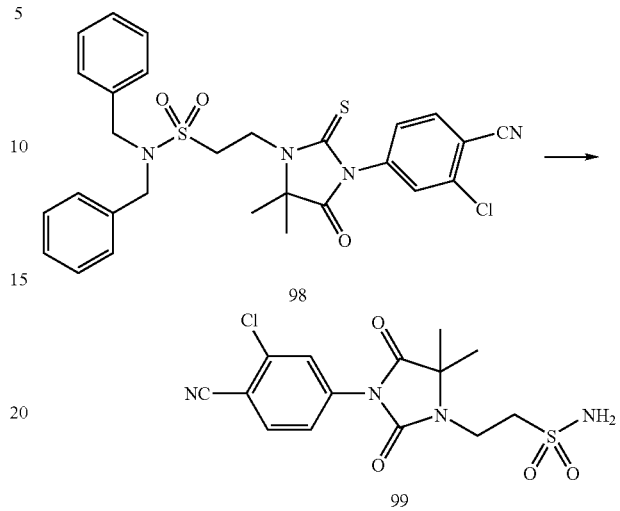

Concentrated sulfuric acid (2.22 mL) was added to compound 98 (74 mg), and the resulting mixture was stirred for 10 minutes at room temperature. The reaction mixture was diluted with water, and an extraction was performed with ethyl acetate. The organic layer washed with a saturated solution of sodium hydrogencarbonate and brine, and was then dried over magnesium sulfate, filtered, and concentrated under reduced pressure. The resulting residue was purified by thin-layer chromatography (developing solvent: hexane: ethyl acetate=1:2) to give 22 mg of the desired compound (compound 99) (yield: 44%).

$^1$H-NMR (400 MHz, CDCl$_3$): 1.62 (6H, s), 3.68 (2H, t, J=7.5 Hz), 4.19 (2H, t, J=7.7 Hz), 4.84 (2H, brs), 7.44 (1H, d, J=8.1 Hz), 7.60 (1H, s), 7.80 (1H, d, J=8.1 Hz).

MS (ESI): 387.0 ([M+H]$^+$).

Example 29

[Formula 74]

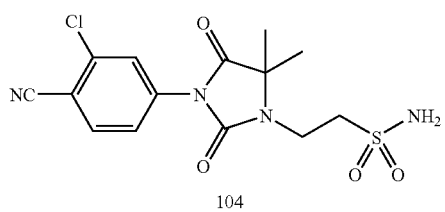

(First Step)

[Formula 75]

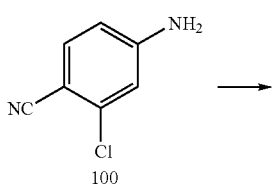

-continued

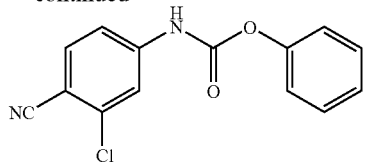
101

Compound 100 (100 mg) was dissolved in tetrahydrofuran (1.3 mL); then, under a nitrogen atmosphere, pyridine (0.066 mL) was added at 0° C., and phenyl chlorocarbonate (0.087 mL) was added dropwise. The reaction solution was stirred for 1 hour while being returned to room temperature. The reaction solution was diluted with ethyl acetate, washed with 1 N hydrochloric acid, water, a saturated solution of sodium hydrogencarbonate and brine, dried over magnesium sulfate, filtered, and concentrated under reduced pressure. The resulting residue was purified by silica gel column chromatography (developing solution: hexane:ethyl acetate=1:0 to 1:1) to give 143.9 mg of the desired compound (compound 101) (yield: 81%).

$^1$H-NMR (400 MHz, CDCl$_3$): 7.17-7.20 (3H, m), 7.26-7.31 (1H, m), 7.41-7.45 (3H, m), 7.63 (1H, d, J=8.4 Hz), 7.79 (1H, s).

Rf value (silica gel plate, developing solvent: hexane:ethyl acetate=1:1): 0.68.

(Second Step)

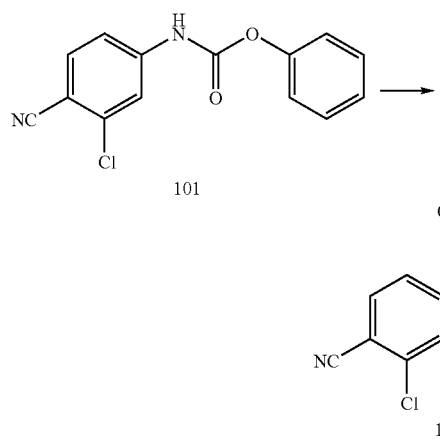

[Formula 76]

2-Aminoisobutyric acid methyl ester hydrochloride (300 mg) was suspended in dichloromethane (22 mL); then, under a nitrogen atmosphere, N-diisopropylethylamine (0.68 mL) was added at 0° C., and the resulting mixture was stirred for 10 minutes, after which compound 101 (620 mg) was added, and the resulting mixture was stirred for 1 hour at room temperature. Next, DBU (0.584 mL) was added, and the resulting mixture was stirred overnight at room temperature. Water was added to the reaction solution, and an extraction was performed with dichloromethane. The organic layer was washed with 1 N hydrochloric acid and a saturated solution of sodium hydrogencarbonate, dried over magnesium sulfate, filtered, and concentrated under reduced pressure. The resulting residue was purified by silica gel column chromatography (developing solvent: hexane:ethyl acetate=1:0 to 1:1) to give 442.2 mg of the desired compound (compound 102) (yield: 86%).

$^1$H-NMR (400 MHz, DMSO-d$_6$): 1.42 (6H, s), 7.70 (1H, d, J=8.4 Hz), 7.92 (1H, s), 8.12 (1H, d, J=8.4 Hz), 8.80 (1H, s).

Rf value (silica gel plate, developing solvent: hexane:ethyl acetate=1:1): 0.32.

(Third Step)

[Formula 77]

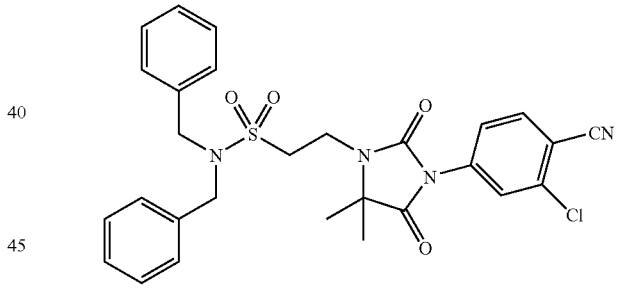

Compound 102 (45.9 mg) was dissolved in N,N-dimethylformamide (1.5 mL); then, sodium hydride (60% in oil, 7.6 mg) was added, and the resulting mixture was stirred for 30 minutes at room temperature. Compound 97 (50 mg) was added, and the resulting mixture was stirred for 2 hours at room temperature. Water was added to the reaction solution, and an extraction was performed with ethyl acetate. The organic layer washed with water and brine, dried over magnesium sulfate, filtered, and concentrated under reduced pressure. The resulting residue was purified by thin-layer chromatography (developing solvent: hexane:ethyl acetate=2:1) to give 67.3 mg of the desired compound (compound 103) (yield: 70%).

MS (ESI): 551.0 ([M+H]$^+$).

Rf value (silica gel plate, developing solvent: hexane:ethyl acetate 3:2): 0.45.

(Fourth Step)

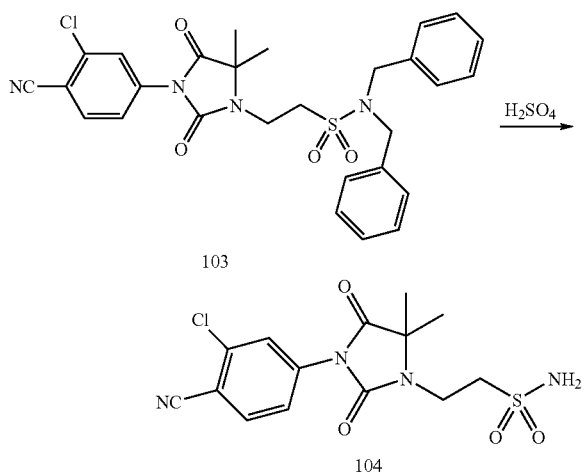

26.3 mg of the desired compound (compound 104) (yield: 58%) was obtained by the same method as in the fourth step of Example 28.

$^1$H-NMR (400 MHz, DMSO-$d_6$): 1.48 (6H, s), 3.30-3.38 (2H, m), 3.68-3.73 (2H, m), 7.06 (2H, s), 7.70 (1H, d, J=8.1 Hz), 7.92 (1H, s), 8.15 (1H, d, J=8.8 Hz).

MS (ESI): 370.9 ([M+H]$^+$).

Rf value (silica gel plate, developing solvent: hexane:ethyl acetate=1:2): 0.10.

Example 30

[Formula 79]

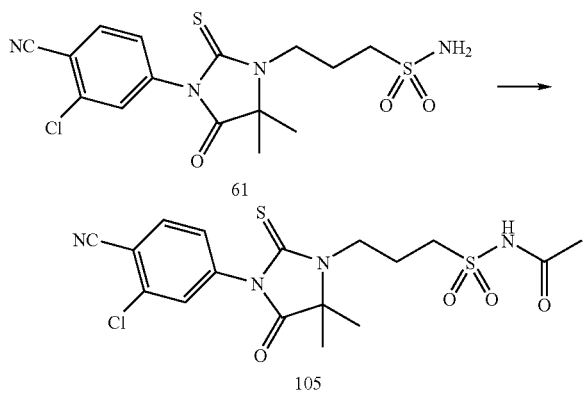

Compound 61 (100 mg) was dissolved in N,N-dimethylformamide (3 mL); then, sodium hydride (60% in oil, 15 mg) was added, and the resulting mixture was stirred for 15 minutes at room temperature. Acetyl chloride (0.0247 mL) was added dropwise, and the resulting mixture was stirred for 1 hour at room temperature. Water was added to the reaction solution, and an extraction was performed with ethyl acetate; then, the organic layer washed with water and brine, dried over magnesium sulfate, and filtered, and concentrated under reduced pressure. The resulting residue was purified by thin-layer chromatography (developing solvent: hexane:ethyl acetate=3:1) to give 15 mg of the desired compound (compound 105) (yield: 14%).

$^1$H-NMR (400 MHz, CDCl$_3$): 1.59 (6H, s), 2.17 (3H, s), 2.39-2.46 (2H, m), 3.57 (2H, t, J=7.0 Hz), 3.90 (2H, t, J=8.1 Hz), 7.44 (1H, d, J=8.1 Hz), 7.61 (1H, s), 7.79 (1H, d, J=8.4 Hz).

MS (ESI): 442.9 ([M+H]$^+$).

Rf value (silica gel plate, developing solvent: hexane:ethyl acetate=1:4): 0.38.

[Preparation of Cells Used in Test Examples]

Preparation of 11A11B2 Cells

HeLa cells (purchased from Dai-Nippon Seiyaku K.K.) were cultured overnight in Dulbecco's Modified Eagle Medium containing no phenol red, but containing 3% charcoal-treated fetal bovine serum (hereafter referred to as DCC-FBS) (this medium is hereafter referred to as phenol-red-free DMEM). An MMTV-Luc-Hyg vector (reporter plasmid with mouse mammary tumor virus long terminal repeat as an androgen response element: vector obtained by substituting the chloramphenicol acetyl transferease gene of a GM-CAT vector (A.T.C.C No. 67282) purchased from the A.T.C.C. with the firefly luciferase gene, and inserting a hygromycin resistance gene as a drug resistance gene), and pSG5-hAR-neo (human androgen receptor expression vector: a vector having an androgen receptor gene under the control of the SV40 promoter, and having a neomycin resistance gene inserted as a drug resistance gene) were transfected into the HeLa cells using an FuGENE™ 6 Transfection Reagent (obtained from Roche).

A clone in which transcription activity was elevated in a dose-dependent manner by dihydrotestosterone was obtained by culturing the transfected cells in DMEM containing 500 µg/mL neomycin, 300 µg/mL hygromycin and 10% fetal bovine serum (hereafter referred to as FBS). The clone cells thus obtained (11A11B2 cells) were maintained and propagated using DMEM containing 400 µg/mL neomycin, 200 µg/mL hygromycin and 10% FBS, and were propagated using phenol-red-free DMEM containing 10% DCC-FBS three to four days prior to the performance of an androgen receptor reporter gene assay.

Test Example 1

Investigation of Agonist Effects of Compounds of the Examples and Compounds of the Comparative Examples The 11A11B2 cells were inoculated in a white clear-bottomed 96-well microplate (COSTAR) so that the cell concentration was $1.0 \times 10^4$/well, using phenol-red-free DMEM containing 3% DCC-FBS (hereafter referred to as the assay medium), and were cultured overnight. The assay medium containing the compounds of the examples and compounds of the comparative examples were added so that the final concentrations of the compounds of the examples and compounds of the comparative examples were 1, 10, 100, 1,000 and 10,000 nmol/L (however, in the case of the compounds of Examples 1 and 2, the compounds were added so that the final concentrations were 1, 10, 100, 1,000, 10,000 and 100,000 mol/L), and the cells were cultured for 48 hours, after which the transcription activity value was measured. The transcription activity was measured using a Bright-Glo™ Luciferase Assay System (Promega).

The transcription activity rates of the compounds of the examples were calculated from the transcription activity measured by the abovementioned method, with the transcription activity value obtained at 0.1 nmol/L DHT taken as 100%, and the transcription activity value in the case of the assay medium alone taken as 0%. The compound concentration showing a transcription activity of 5% (EC5 value) was calculated from a linear equation for two points on either side of 5%.

Test Example 2

Investigation of Antagonist Effects of Compounds of the Examples and Compounds of the Comparative Examples The 11A11B2 cells were inoculated in a white clear-bottomed 96-well microplate (COSTAR) so that the cell concentration was $1.0 \times 10^4$/well, using the assay medium, and were cultured overnight. The assay medium containing DHT was added so that the final concentration of DHT was 0.1 nmol/L, and the assay medium containing the compounds of the examples or compounds of the comparative examples were added so that the final concentrations of the compounds of the examples or compounds of the comparative examples were 1, 10, 100, 1,000 and 10,000 nmol/L, respectively. After culturing for 48 hours, the transcription activity values were measured. The transcription activity was measured using a Bright-Glo™ Luciferase Assay System (Promega).

The transcription activity rates of the compounds of the examples were calculated from the transcription activity measured by the abovementioned method, with the transcription activity value obtained at 0.1 nmol/L DHT taken as 100%, and the transcription activity value in the case of the assay medium alone taken as 0%.

In the present test system (Test Example 2), there were cases in which the transcription activity dropped to 50% in compounds having both antagonist activity and agonist activity. Accordingly, the value obtained by subtracting the transcription activity rate of Test Example 1 (Investigation of Agonist Activity) from the transcription activity rate of Test Example 2 (Investigation of Antagonist Activity) was used to calculate the compound concentration at which a transcription activity of 50% was shown (IC50 value). The IC50 value was calculated from a linear equation for two points on either side of 50%.

A procedure of an assay relating to Test Examples 1 and 2 are disclosed in the following documents:

Rapid and sensitive reporter gene assays for detection of antiandrogenic and estrogenic effects of environmental chemicals: A. M. Vinggaard et al., Toxicol. Appl. Pharmacol. 1999 Mar. 1; 155(2); 150-160; and A new luciferase reporter gene assay for the detection of androgenic and antiandrogenic effects based on a human prostate specific antigen promoter and PC3/AR human prostate cancer cells: R. Kizu et al., Anal. Sci. 2004 January; 20(1); 50-59.

The results of Test Examples 1 and 2 are shown in Table 3.

TABLE 3

| Compound | EC5(nM) | IC50(nM) | EC5/IC50 |
|---|---|---|---|
| Compound of Example 1 | >10000 | 200 | >50 |
| Compound of Example 2 | >10000 | 300 | >33 |
| Compound of Example 3 | 2000 | 100 | 20 |
| Compound of Example 26 | >10000 | 900 | >11 |
| Compound of Example 27 | >10000 | 400 | >25 |
| Compound of Example 28 | >10000 | 400 | >25 |
| Comparative Example 1 | 0.08 | 1 | 0.080 |
| Comparative Example 2 (BP-139) | 3000 | 800 | 3.8 |
| Comparative Example 3 (bicalutamide) | 20 | 300 | 0.067 |
| Comparative Example 4 (hydroxyflutamide) | 10 | 100 | 0.1 |

Comparative Example 1

Compound of Example 12 in Japanese Patent Application Laid-Open No. 4-308579 (4-(5-oxo-2-thioxo-3,4,4-trimethyl-1-imidazolidinyl)-2-trifluoromethylbenzonitrile)

Comparative Example 2

Compound of Example 15 in Japanese Patent Publication No. 10-510845 ((4-[3'-(2"-N-acetylaminoethyl)-4',4'-dimethyl-5'-oxo-2'-thioxo-1'-imidazolidinyl]-2-trifluoromethylbenzonitrile)

Comparative Examples 3 and 4 are publicly known compounds, and can be manufactured by universally known methods.

The effect as an anti-androgen agent with reduced agonist activity can be assessed by comparing the EC5/IC50 values. Specifically, compounds that have a high EC5/IC50 value are compounds that have a more desirable effect. In concrete terms, it is desirable that the EC5/IC50 value be 5 or greater, preferably 10 or greater, and even more preferably 20 or greater.

In Test Examples 1 and 2, it was confirmed that the compounds expressed by formula (I) of the present invention have EC5/IC50 values that are clearly higher than those of the compounds of the comparative examples.

INDUSTRIAL APPLICABILITY

It is expected that the compounds of the present invention represented by formula (I) will act as anti-androgen agents that show no manifestation of androgen resistance due to long-term administration, and/or side effects such as liver toxicity or the like. Furthermore, it is expected that these compounds will be useful in pharmaceutical compositions, e.g., therapeutic agents for disorders such as prostate cancer, benign prostatic hypertrophy, male pattern baldness, sexual precociousness, common acne, seborrhea, hypertrichosis and the like. Furthermore, it is expected that the compounds of the present invention represented by general formula (I) will prevent or delay the onset of disorders such as prostate cancer, benign prostatic hypertrophy, male pattern baldness, sexual precociousness, common acne, seborrhea, hypertrichosis and the like, if these compounds are administered in advance. Accordingly, it is expected that these compounds will act as prophylactic agents for such disorders.

The invention claimed is:

1. A compound represented by formula (I):

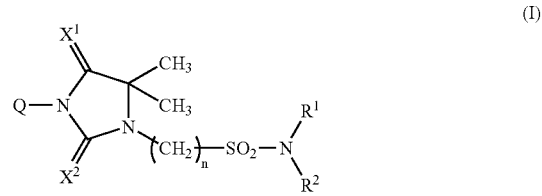

wherein, n is an integer selected from 1 to 20, Q is

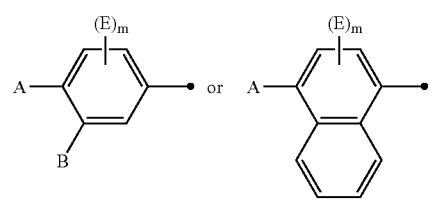

A is cyano group, —COOR³, —CONR³R⁴, a $C_1$-$C_4$ alkyl group which may be substituted by one or more halogen atoms, or a nitro group;

B is a hydrogen atom, a halogen atom, —OR³ or a $C_1$-$C_4$ alkyl group which may be substituted by one or more halogen atoms;

$X^1$ and $X^2$ are independently selected from O and S;

m is an integer selected from 0 to 3;

E is independently a $C_1$-$C_4$ alkyl group;

$R^1$ and $R^2$ are independently selected from a hydrogen atom, a $C_1$-$C_6$ alkyl group, and a $C_1$-$C_6$ alkylcarbonyl group;

$R^3$ and $R^4$ are independently selected from a hydrogen atom and a $C_1$-$C_6$ alkyl group;

with the proviso that when $X^1$ is O and $X^2$ is S, Q is not 4-cyano-3-trifluoromethylphenyl group, or a pharmaceutically acceptable salt, or a prodrug thereof.

2. A compound according to claim 1 or a pharmaceutically acceptable salt, or a prodrug thereof, wherein A is trifluoromethyl group, cyano group, carboxy group, carbamoyl group, N-methylcarbamoyl group, N,N-dimethylcarbamoyl group, or nitro group.

3. A compound according to claim 1 or a pharmaceutically acceptable salt, or a prodrug thereof, wherein B is a hydrogen atom, trifluoromethyl group, methyl group, ethyl group, a chlorine atom or methoxy group.

4. A compound according to claim 1 or a pharmaceutically acceptable salt, or a prodrug thereof, wherein $X^1$ is O, and $X^2$ is O or S.

5. A compound according to claim 1 or a pharmaceutically acceptable salt, or a prodrug thereof, wherein n is an integer selected from 1 to 10.

6. A compound according to claim 1 or a pharmaceutically acceptable salt, or a prodrug thereof, wherein $R^1$ and $R^2$ are hydrogen atoms.

7. A compound according to claim 1 or a pharmaceutically acceptable salt, or a prodrug thereof, wherein at least one of $R^1$ and $R^2$ is a methyl group or acetyl group.

8. A compound according to claim 1 or a pharmaceutically acceptable salt, or a prodrug thereof, wherein $R^3$ and $R^4$ are each independently selected from a hydrogen atom and methyl group.

9. A compound according to claim 1 or a pharmaceutically acceptable salt, or a prodrug thereof, which are selected from the group consisting of:

3-[3-(3-chloro-4-cyanophenyl)-5,5-dimethyl-4-oxo-2-thioxoimidazolidin-1-yl]propane-1-sulfonic acid amide;

3-[3-(4-cyano-3-methoxyphenyl)-5,5-dimethyl-4-oxo-2-thioxoimidazolidin-1-yl]propane-1-sulfonic acid amide;

3-[3-(4-cyano-2-methyl-3-trifluoromethylphenyl)-5,5-dimethyl-4-oxo-2-thioxoimidazolidin-1-yl]propane-1-sulfonic acid amide;

3-[3-(4-cyano-2-methyl-5-trifluoromethylphenyl)-5,5-dimethyl-4-oxo-2-thioxoimidazolidin-1-yl]propane-1-sulfonic acid amide;

3-[3-(4-nitro-3-trifluoromethylphenyl)-5,5-dimethyl-4-oxo-2-thioxoimidazolidin-1-yl]propane-1-sulfonic acid amide;

3-[3-(4-cyano-3-methylphenyl)-5,5-dimethyl-4-oxo-2-thioxoimidazolidin-1-yl]propane-1-sulfonic acid amide;

3-[3-(4-cyano-3-ethylphenyl)-5,5-dimethyl-4-oxo-2-thioxoimidazolidin-1-yl]propane-1-sulfonic acid amide;

3-[3-(3-methyl-4-nitrophenyl)-5,5-dimethyl-4-oxo-2-thioxoimidazolidin-1-yl]propane-1-sulfonic acid amide;

3-[3-(4-trifluoromethylnaphth-1-yl)-5,5-dimethyl-4-oxo-2-thioxoimidazolidin-1-yl]propane-1-sulfonic acid amide;

3-[3-(4-cyanophenyl)-5,5-dimethyl-4-oxo-2-thioxoimidazolidin-1-yl]propane-1-sulfonic acid amide;

3-[3-(4-carboxyphenyl)-5,5-dimethyl-4-oxo-2-thioxoimidazolidin-1-yl]propane-1-sulfonic acid amide;

3-[3-(4-aminocarbonylphenyl)-5,5-dimethyl-4-oxo-2-thioxoimidazolidin-1-yl]propane-1-sulfonic acid amide;

3-[3-{4-(N,N-dimethylaminocarbonyl)phenyl}-5,5-dimethyl-4-oxo-2-thioxoimidazolidin-1-yl]propane-1-sulfonic acid amide;

3-[3-(4-carboxy-3-trifluoromethylphenyl)-5,5-dimethyl-4-oxo-2-thioxoimidazolidin-1-yl]propane-1-sulfonic acid amide;

3-[3-(4-aminocarbonyl-3-trifluoromethylphenyl)-5,5-dimethyl-4-oxo-2-thioxoimidazolidin-1-yl]propane-1-sulfonic acid amide;

3-[3-{4-(N,N-dimethylaminocarbonyl)-3-trifluoromethylphenyl}-5,5-dimethyl-4-oxo-2-thioxoimidazolidin-1-yl]propane-1-sulfonic acid amide;

3-[3-(4-cyanonaphth-1-yl)-5,5-dimethyl-4-oxo-2-thioxoimidazolidin-1-yl]propane-1-sulfonic acid amide;

3-[3-(4-nitronaphth-1-yl)-5,5-dimethyl-4-oxo-2-thioxoimidazolidin-1-yl]propane-1-sulfonic acid amide;

3-[3-(4-aminocarbonylnaphth-1-yl)-5,5-dimethyl-4-oxo-2-thioxoimidazolidin-1-yl]propane-1-sulfonic acid amide;

3-[3-{4-(N,N-dimethylaminocarbonyl)naphth-1-yl}-5,5-dimethyl-4-oxo-2-thioxoimidazolidin-1-yl]propane-1-sulfonic acid amide;

3-[3-(3-chloro-4-cyanophenyl)-5,5-dimethyl-2,4-dioxoimidazolidin-1-yl]propane-1-sulfonic acid amide;

3-[3-(4-cyano-3-methoxyphenyl)-5,5-dimethyl-2,4-dioxoimidazolidin-1-yl]propane-1-sulfonic acid amide;

3-[3-(4-cyano-2-methyl-3-trifluoromethylphenyl)-5,5-dimethyl-2,4-dioxoimidazolidin-1-yl]propane-1-sulfonic acid amide;

3-[3-(4-cyano-2-methyl-5-trifluoromethylphenyl)-5,5-dimethyl-2,4-dioxoimidazolidin-1-yl]propane-1-sulfonic acid amide;

N-methyl-3-[3-(3-chloro-4-cyanophenyl)-5,5-dimethyl-4-oxo-2-thioxoimidazolidin-1-yl]propane-1-sulfonic acid amide;

4-[3-(3-chloro-4-cyanophenyl)-5,5-dimethyl-4-oxo-2-thioxoimidazolidin-1-yl]butane-1-sulfonic acid amide;

5-[3-(3-chloro-4-cyanophenyl)-5,5-dimethyl-4-oxo-2-thioxoimidazolidin-1-yl]pentane-1-sulfonic acid amide;

2-[3-(3-chloro-4-cyanophenyl)-5,5-dimethyl-4-oxo-2-thioxoimidazolidin-1-yl]ethane-1-sulfonic acid amide;

2-[3-(3-chloro-4-cyanophenyl)-5,5-dimethyl-2,4-dioxoimidazolidin-1-yl]ethane-1-sulfonic acid amide; and N-acetyl-3-[3-(3-chloro-4-cyanophenyl)-5,5-dimethyl-4-oxo-2-thioxoimidazolidin-1-yl]propane-1-sulfonic acid amide.

10. A pharmaceutical composition which contains the compound according to claim 1 or a pharmaceutically acceptable salt, a prodrug thereof as an active ingredient.

11. A process for preparing a compound represented by formula (I):

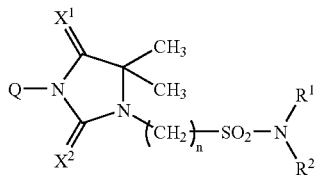

wherein, Q, $X^1$, $X^2$, n, $R^1$ and $R^2$ are as described in claim 1, comprising steps of:

reacting a compound represented by formula (II):

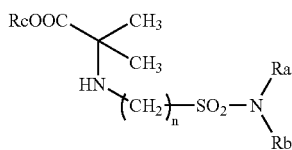

wherein n is an integer selected from integers of 1 to 20;

Ra and Rb are each independently selected from a $C_1$-$C_6$ alkyl group substituted by one or more $W^1$, a $C_1$-$C_6$ alkylcarbonyl group which may be substituted by one or more $W^1$, an arylcarbonyl group which may be substituted by one or more $W^2$, a $C_1$-$C_6$ alkoxycarbonyl group which may be substituted by one or more $W^1$, an aryloxycarbonyl group which may be substituted by one or more $W^2$, a $C_1$-$C_6$ alkylaminocarbonyl group which may be substituted by one or more $W^1$, a di($C_1$-$C_6$ alkyl) aminocarbonyl group which may be substituted by one or more $W^1$, a $C_1$-$C_6$ alkylsulfonyl group which may be substituted by one or more $W^1$, and an arylsulfonyl group which may be substituted by one or more $W^2$, and $R^1$ and $R^2$; or Ra and Rb may be joined together to form a group =CH—$W^3$;

$W^1$ is a $C_1$-$C_6$ alkoxy group, a $C_1$-$C_6$ alkylthio group, a $C_1$-$C_6$ alkylsulfynyl group, a $C_1$-$C_6$ alkylsulfonyl group, an aryl group which may be substituted by one or more $W^2$, an aryloxy group which may be substituted by one or more $W^2$, or a $C_7$-$C_{14}$ aralkyloxy group which may be substituted by one or more $W^2$;

$W^2$ is a $C_1$-$C_6$ alkyl group, a $C_1$-$C_6$ alkoxy group, a $C_1$-$C_6$ haloalkyl group, a halogen atom, cyano group, or nitro group;

$W^3$ is a $C_1$-$C_6$ alkyl group, a $C_1$-$C_6$ alkoxy group, a $C_1$-$C_6$ alkylamino group, a di($C_1$-$C_6$ alkyl)amino group;

$R^1$ and $R^2$ are as defined in claim 1; and

Rc is a $C_1$-$C_6$ alkyl group, with a compound represented by the following formula (IV):

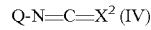

wherein, Q and $X^2$ are as defined in claim 1, to obtain a compound represented by formula (III):

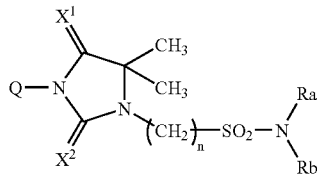

wherein, Q, $X^1$, $X^2$, n, Ra and Rb are as described hereinbefore; and a deprotection in cases where at least one of the groups Ra and Rb is other than $R^1$ and $R^2$.

12. A compound represented by formula (III):

[Formula 6]

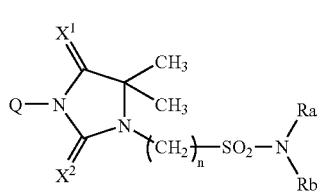

wherein, Q, $X^1$, $X^2$ n, Ra and Rb are as defined in cm 11.

* * * * *